United States Patent [19]

Heilmann et al.

[11] Patent Number: 5,292,840
[45] Date of Patent: Mar. 8, 1994

[54] POLYMERIC SUPPORTS

[75] Inventors: Steven M. Heilmann, Afton; Jerald K. Rasmussen, Stillwater; Larry R. Krepski, White Bear Lake; Dean S. Milbrath, Stillwater; Patrick L. Coleman, Minneapolis; Margaret M. Walker, Apple Valley, all of Minn.

[73] Assignee: Minnesota Mining and Manufacturing Company, St. Paul, Minn.

[21] Appl. No.: 335,835

[22] Filed: Apr. 10, 1989

Related U.S. Application Data

[63] Continuation-in-part of Ser. No. 158,258, Feb. 19, 1988, Pat. No. 4,871,824, which is a continuation-in-part of Ser. No. 25,605, Mar. 13, 1987, Pat. No. 4,737,560.

[51] Int. Cl.$^5$ .................... C08F 20/58; C08F 22/38
[52] U.S. Cl. .................... 526/304; 526/306
[58] Field of Search ............... 525/326.8, 326.9, 279; 526/304, 306

[56] References Cited

U.S. PATENT DOCUMENTS

| | | | |
|---|---|---|---|
| 3,511,894 | 5/1970 | Markert | 526/260 |
| 3,583,950 | 6/1971 | Kollinsky | 526/260 |
| 4,070,348 | 1/1978 | Kraemer et al. | 260/79.3 |
| 4,157,418 | 6/1979 | Heilmann | 526/304 |
| 4,190,713 | 2/1980 | Kraemer et al. | 521/149 |
| 4,208,309 | 6/1980 | Kraemer et al. | 260/8 |
| 4,224,427 | 9/1980 | Mueller | 526/260 |
| 4,378,411 | 3/1983 | Heilmann et al. | 428/500 |
| 4,451,619 | 5/1984 | Heilmann et al. | 525/379 |
| 4,619,867 | 10/1986 | Charbonneau | 526/260 |
| 4,694,103 | 9/1987 | Krepski et al. | 562/450 |

OTHER PUBLICATIONS

J. K. Rasmussen, et al., "Polyazlactones", *Encylcopedia of Polymer Science and Engineering*, vol. 11, 1988, New York, pp. 558–571.

G. L. Stahl et al., "An Entirely Beaded Poly(Dimethylacrylamide) Support For Peptide Synthesis", *The*

(List continued on next page.)

Primary Examiner—Joseph L. Schofer
Assistant Examiner—Wu C. Cheng
Attorney, Agent, or Firm—Gary L. Griswold; Walter N. Kirn; Lorraine R. Sherman

[57] ABSTRACT

Azlactone-functional polymer supports are useful reactive supports for the attachment of functional materials to provide novel adduct beads. The adduct beads are useful as complexing agents, catalysts, polymeric reagents, chromatographic supports, and as enzyme- or other biologically active supports. Novel carboxylate-functional polymer beads, are intermediates in the preparation of the azlactone-functional beads.

Azlactone-functional supports have units of the formula:

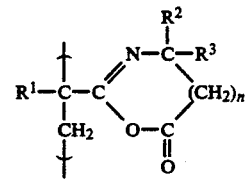

wherein
R$^1$ is H or CH$_3$,
R$^2$ and R$^3$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or R$^2$ and R$^3$ taken together with the carbon to which they are joined can form a carbocyclic ring containing 4 to 12 ring atoms, and
n is an integer 0 or 1,
the azlactone functional supports having 0.1 to 99 molar parts of crosslinking monomer incorporated therein.

10 Claims, No Drawings

OTHER PUBLICATIONS

*Journal of Organic Chemistry*, vol. 44, No. 19, Sep. 14, 1979, pp. 3424–3425.

D. I. Hoke et al., "Preparation and Polymerization of 3-acrylamido-3-methylbutanoic Acid", *Journal of Polymer Science: Polymer Chemistry Edition*, vol. 10, No. 11, Nov. 1972, New York, pp. 3311–3315.

R. B. Merrifield, *J. Am. Chem. Soc.*, 85, 2149 (1963).

N. K. Mathur, C. K. Narang, and R. E. Williams, *Polymers as Aids in Organic Chemistry*, Chapter 2, Academic Press, New York (1980).

L. D. Taylor et al., *Makromol. Chem. Rapid Commun.*, 3, 779 (1982).

U.S. Ser. No. 07/335,284, filed Apr. 10, 1989.

POLYMERIC SUPPORTS

This application is a continuation-in-part of U.S. Ser. No. 07/158,258 filed Feb. 19, 1988, 4,871,824, which was a continuation-in-part of U.S. Ser. No. 07/025,605, filed Mar. 13, 1987, U.S. Pat. No. 4,737,560.

FIELD OF THE INVENTION

This invention relates to azlactone-functional supports, including polymer beads, membranes, films, and coatings. The azlactone-functional supports are useful for attachment of functional materials to provide novel adduct supports. The adduct supports are useful as complexing agents, catalysts, and polymeric reagents, as enzyme or other protein-bearing supports, and as chromatographic supports. In additional aspects, methods of preparation of the supports are disclosed.

BACKGROUND OF THE INVENTION

The attachment of useful materials such as catalysts, reagents, chelating or complexing agents, and proteins to insoluble supports is well-known. With the attending advantages of ease of removal and recovery from the system, e.g., by simple filtration, regeneration (if necessary), and recycling coupled with the increased utilization of continuous flow systems in both general chemical processing and diagnostic monitoring procedures, supported materials are ubiquitous in today's technology. One indication of this is the listing of "Polymer-Supported Reagents" as a separate heading in the General Subjects Index of *Chemical Abstracts* beginning in 1982.

Concerning the nature of the insoluble support material, both inorganic polymers (notably silica gel and alumina) and organic polymers have been utilized. Factors, however, such as increased capacity because of better porosity (especially with the so-called "gel-type" polymers which swell somewhat and allow relatively free access by solvent and solute to the bound functionality within the support) and better control of the polar nature of the support (by selection of appropriate comonomers), which has been shown to directly affect reaction rate, have led to a general preference for the organic polymer supports. Polystyrene has been the solid support material most extensively utilized.

The attaching functionality for polystyrene supports most often utilized has been the chloromethylphenyl group. These reactive, solid supports are the so-called "Merrifield resins", so named for R. B. Merrifield (*J. Am. Chem. Soc.*, 85, 2149 (1963)) who received the Nobel Prize in Chemistry in 1984 for these and other achievements. Merrifield resins are extremely useful for conducting solid phase peptide syntheses, but their broad utilization as reactive, solid supports is limited because of the relative nonpolarity of the hydrophobic polystyrene backbone, an oftentimes unpredictable attaching reaction which involves nucleophilic displacement of chloride ion, and a relatively low capacity of reactable chloromethylphenyl groups per gram of polymer. The chloromethylphenyl and other reactive functionalities are discussed by N. K. Mathur, C. K. Narang, and R. E. Williams, "Polymers as Aids in Organic Chemistry", Chapter 2, Academic Press: New York (1980).

The present state of reactive, insoluble supports may be summarized by the statement that no one support is broadly suitable for the many applications of solid-supported materials. The spectrum of properties required varies tremendously depending on the end-use, which includes such diverse applications as mediating organic synthetic transformations, removing precious metals from sea water or heavy metal contaminants from industrial effluents, utilizing supported metals as catalysts for conducting organic reactions and polymerizations, resolving optical isomers, separating biomacromolecules, and attaching biomacromolecules.

Azlactones have not been previously utilized as attaching groups on insoluble supports. Azlactones have, however, been proposed to be useful in two instances.

U.S. Pat. No. 4,070,348 teaches the preparation of water-swellable, crosslinked bead copolymers having 0.2 to 5 mol percent crosslinking monomer and at least 10 mole percent of a water soluble comonomer incorporated therein. The copolymers are reactive with proteins primarily by the inclusion of oxirane groups which are the only reactive groups claimed. Several "activated carboxyl groups" (col. 4; line 42), however, are listed including a 2-alkenyl azlactone, 2-isopropenyl-4,4-dimethyl-oxazolone-5 (col. 5; lines 2-3), and reaction of this compound with a primary amino group of a protein is depicted schematically (col. 5; lines 6-14). No additional information or enabling disclosure is given about incorporation of the azlactone into a hydrophilic, crosslinked bead copolymer or reaction of an azlactone-functional insoluble support with a protein or any other functional material. The crosslinked, bead copolymers of U.S. Pat. No. 4,070,348 are all prepared purposely in essentially an anhydrous condition, i.e. with care being taken to exclude water.

L. D. Taylor, et al., *Makromol. Chem., Rapid Commun.*, 3, 779 (1982) have proposed azlactones to be useful as reactive groups on polymeric supports. Only the bulk homopolymerization of 2-vinyl-4,4-dimethylazlactone to form a polymeric "plug" is described. No mention of crosslinking and generation of polymeric beads is given. Furthermore, described at some length is the susceptibility of the poly(azlactone) to hydrolysis, i.e., ring-opening reaction with water [equation (1)]. Hydrolysis is regarded as being very facile, occurring even with traces of moisture often present in organic solvents for the homopolymer, as follows:

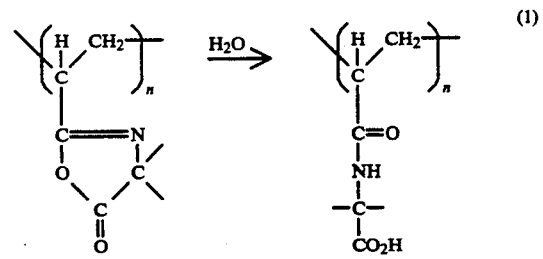

Based on this account of the propensity toward hydrolysis, it is entirely unexpected that an azlactone-functional support could be selectively reacted with a functional material in aqueous media.

SUMMARY OF THE INVENTION

Briefly, the present invention provides hydrophilic azlactone-functional supports, including polymer beads, membranes, films, and coatings, having in the range of 0 to 99 molar parts of crosslinking monomer incorporated therein.

In another aspect, the present invention provides novel adduct supports which are produced by a ring opening reaction between the azlactone-functional supports of the invention and functional materials. The adduct supports are useful as complexing agents, catalysts, reagents, adsorbants, chromatographic supports, and as biologically active supports.

The present invention provides four methods for the preparation of supports of the invention. Several methods are available for preparing azlactone-functional supports. One method is to apply alkenyl azlactone monomer to the support (optionally along with other co-monomers) and polymerize the monomer(s) in place, e.g., by photopolymerization (utilizing an appropriate photoinitiator).

In Process I carboxylate-functional polymer supports are prepared as intermediates to azlactone-functional polymer supports by the reverse phase suspension polymerization product of:

(i) optionally, at least one free radically addition polymerizable, water soluble monomer, (ii) at least one water-soluble salt of an N-(meth)acryloylamino acid, and (iii) at least one crosslinking monomer.

Reaction of a cyclization agent and the carboxylate-functional polymer supports just described provides azlactone-functional polymer supports.

In Process II of the invention the azlactone-functional supports can be prepared by the reverse phase suspension polymerization product of (i) optionally, at least one free radically addition polymerizable, water soluble monomer, (ii) at least one alkenyl azlactone, and (iii) at least one crosslinking monomer.

In Process III of the invention the azlactone-functional supports can be prepared by the dispersion polymerization reaction product of (i) optionally, at least one free radically addition polymerizable monomer, (ii) at least one alkenyl azlactone, and (iii) optionally, at least one crosslinking monomer.

In Process IV of the invention azlactone-functional supports can be provided by coating an azlactone-functional polymer onto a solid support.

Reaction of the azlactone-functional supports of the invention with functional materials capable of reacting with the azlactone ring (i.e, by a ring-opening reaction) provides the adduct supports of the invention. We have discovered that this adduct-forming reaction occurs to a high degree with a dissolved nucleophile in water solution, especially when the nucleophile is primary amine-functional. This selectivity of reaction is even more surprising when one considers that the concentration of the amine nucleophile on a protein functional material, for example, is most often substantially lower than that of the water solvent. Before the present invention, it was thought that azlactone groups would predominantly react with water, i.e., hydrolyze, rather than react with a dissolved nucleophile.

The hydrophilic or hydrophobic nature of a support is extremely important in determining its utility. An obvious advantage of a hydrophilic support is that many of the operations of supported materials are conducted in aqueous media. Water is virtually the exclusive solvent for conducting precious or noxious metal ion removal, in diagnostic monitoring of components of biofluids and biosystems, as well as in a number of chemical reactions, and it is oftentimes advantageous to utilize a polymer support which will swell in water. The water solvent can facilitate the additional encounter and interaction of a solute and reactive groups within the hydrophilic support as well as at the support-water interface.

Hydrophilic polymer-supported materials find use and are beneficial in non-aqueous systems as well. Functional groups which impart hydrophilicity are highly polar in nature, and supported material functions which are sensitive to solvent effects will be tremendously affected, especially in terms of rate, by the polarity of the polymer backbone. Importance of the polymer backbone in determining the local environment for a supported material has been noted by H. Morawetz, *J. Macromol. Sci.—Chem.*, A-13, 311 (1979).

As has been noted above, U.S. Pat. No. 4,070,348 discloses water-swellable, crosslinked bead copolymers having 0.2 to 5 mol percent crosslinking monomer and at least 10 mole percent of a water soluble comonomer incorporated therein. The patentee desires beads having a high degree of swelling in water, i.e., 5–100 times as is disclosed in col. 6, lines 66–67. This high degree of swelling is deemed important to achieve high binding capacity with proteins. In col. 9, lines 30–32, of U.S. Pat. No. 4,070,348, it is stated that "The greatest part of the biologically active substances are found in the wide mesh 'hollow spaces' within the swollen particles."

However, many applications, particularly chromatographic applications, cannot conveniently utilize support materials which exhibit a high degree of swelling in aqueous media.

Surprisingly, we have now found that azlactone beads having remarkably high binding capacity with functional materials can be achieved with highly crosslinked beads which swell very modestly, e.g., threefold or less, in water. When, desired, a high degree of crosslinking is achieved by incorporating greater than 5 and up to 99 molar parts (mol percent) crosslinking monomer, preferably 7 to 99 molar parts, more preferably 10 to 99 molar parts, and most preferably 30 to 99 molar parts of at least one crosslinking monomer into the azlactone-functional polymer beads.

In this application:

"azlactone-functional support" means an article comprising an azlactone-functional polymer or an azlactone-functional polymer coated on at least one surface of a substrate;

"acryloyl" means not only 1-oxo-2-propenyl but also 1-oxo-2-methyl-2-propenyl resulting from methacryloylation reactions;

"alkyl" means the monovalent residue remaining after removal of a hydrogen atom from a saturated linear or branched chain hydrocarbon having 1 to 14 carbon atoms;

"aryl" means the monovalent residue remaining after removal of one hydrogen atom from an aromatic or heteroaromatic compound which can consist of one ring or two fused or catenated rings having 5 to 12 ring atoms which can include up to 3 heteroatoms selected from S, N, and nonperoxidic O. The carbon atoms can be substituted by up to three halogen atoms, $C_1$–$C_4$ alkyl, $C_1$–$C_4$ alkoxy, N,N-di($C_1$–$C_4$ alkyl)amino, nitro, cyano, and $C_1$–$C_4$ alkyl carboxylic ester;

"arenyl" means the monovalent residue remaining after removal of a hydrogen atom from the alkyl portion of a hydrocarbon containing both alkyl and aryl groups having 6 to 26 carbon and heteroatoms (wherein the heteroatoms are up to 3 S, N, and nonperoxidic O atoms);

"azlactone" means 2-oxazolin-5-one groups of Formula I and 2-oxazin-6-one groups of Formula II;

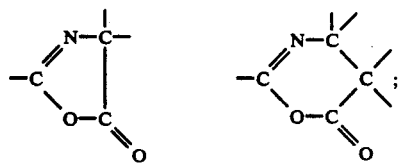

I        II

"parts" means parts by weight unless otherwise specified;

"carboxylate" means

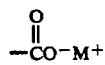

wherein M is hydrogen ammonium, or an alkali metal such as Li, Na, or K;

"macroporous" refers to crosslinked polymers in which the level of crosslinker or difunctional monomers is greater than 20 parts, with no polymer non-solvent or porogen utilization being required;

"biologically active" refers to substances which are biochemically, immunochemically, physiologically or pharmaceutically active such as antibodies, antigenic substances, enzymes, cofactors, inhibitors, lectins, hormones, receptors, coagulation factors, amino acids, histones, vitamins, drugs, cell surface markers, and substances which interact with them;

"gel-type" refers to crosslinked polymers in which the level of crosslinkers or difunctional monomers is less than 20 parts.

Structures and formulae depicted between parentheses are partial structures of polymers.

DETAILED DESCRIPTION OF THE INVENTION

The present invention provides azlactone-functional supports having on at least one of their surfaces units of Formula V:

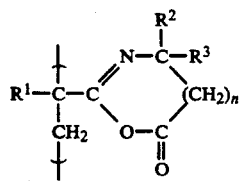

wherein $R^1$ is H or $CH_3$, $R^2$ and $R^3$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or $R^2$ and $R^3$ taken together with the carbon to which they are joined can form a carbocyclic ring containing 4 to 12 ring atoms, and n is an integer 0 or 1.

These supports may be crosslinked azlactone-functional polymeric beads or they may be solid substrates coated on at least one surface with a layer of an azlactone-functional polymer. This layer may have a thickness in the range of 1 nanometer to 5 mm. Useful solid substrates include inorganic solids such as glass, ceramics, unfired metal and nonmetal oxides, clays, zeolites, and organic polymers.

Also provided by this invention are adduct supports having the formula

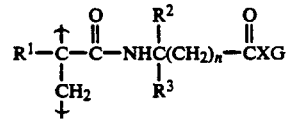

wherein $R^1$, $R^2$, $R^3$, and n are as previously defined,

X can be —O—, —S—, —NH—, or

wherein $R^4$ can be alkyl or aryl, and

G is the residue of HXG which performs the adsorbing, complexing, catalyzing, separating, or reagent function of the adduct beads.

HXG can be a biologically active substance, dye, catalyst, reagent, and the like.

The azlactone-functional supports of this invention are provided by one of several processes:

PROCESS I

Two-step Reverse Phase Suspension Polymerization

The polymer and adduct supports of Process I of the invention can be provided according to the process depicted by Chemical Equations I, below.

CHEMICAL EQUATIONS (PROCESS I) I

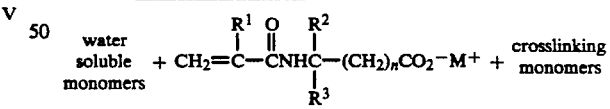

N-acryloylamino acid salt

III

↓ step 1

carboxylate-functional supports

IV.

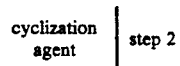

-continued
CHEMICAL EQUATIONS (PROCESS I) I

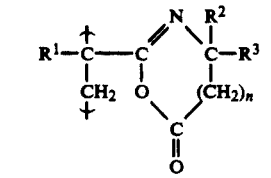

azlactone-functional supports
V functional material HXG | step 3

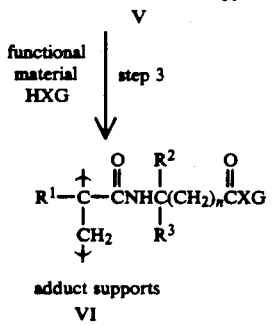

adduct supports
VI

The crosslinked hydrophilic, azlactone-functional polymer beads of Formula V are prepared by a novel two-step process. In the first step the following group of monomers is subjected to a free radical polymerization reaction:

i) 0 to 89 molar parts of at least one water soluble monomer;

ii) 1 to 99.9 molar parts of at least one water soluble salt of N-(meth)acryloylamino acid; and iii) in the range of 0.1 to 99 molar parts, preferably 7 to 99, more preferably 10 to 99, and most preferably 30 to 99 molar parts, of at least one crosslinking monomer.

The product of the above polymerization reaction is the crosslinked, hydrophilic, carboxylate-functional supports of Formula IV. The second step of the process involves treating the carboxylate-functional supports with a cyclization agent to form the azlactone-functional supports of the invention.

The degree of hydrophilicity of the polymer support is largely determined by the amount of water soluble monomer employed, although some hydrophilicity is imparted by the crosslinker and by the functional groups created, i.e., amide-amide, amide-ester, or amide-thiolester with amine, alcohol, or thiol nucleophiles (HXG as defined above), by the ring-opening, azlactone/nucleophile reaction (step 3 of Chemical Equations I). Therefore, in the strictest sense of the present invention, inclusion of a water soluble monomer is optional. Suitable water soluble monomers exhibit a solubility of at least 3 parts in 100 parts water. Preferred monomers include vinyl group-containing and acryloyl group-containing compounds. A representative list of such monomers includes acrylamide, methacrylamide, N,N-dimethylacrylamide, diacetoneacrylamide, N-vinylpyrrolidone, hydroxyethyl methacrylate, 2-acrylamido-2-methylpropanesulfonic acid and its salts, N-(3-methacrylamidopropyl)-N,N,N-trimerhylammonium salts, N,N-dimethylaminoethyl methacrylate, acrylic acid, methacrylic acid, itaconic acid, and combinations thereof. Preferred water soluble monomers are N,N-dimethylacrylamide and N-vinylpyrrolidone.

The N-acryloylamino acid salt monomers include ammonium, sodium, potassium, and lithium salts of N-acryloylamino acids of Formula VII and are prepared by mixing (at <30° C.) equal molar quantities of aqueous solutions of, for example, ammonium hydroxide, sodium hydroxide, potassium hydroxide, or lithium hydroxide and the Formula VII compounds.

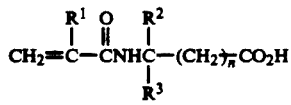

wherein $R^1$, $R^2$, $R^3$, and n are as previously defined.

The N-acryloylamino acid compounds are well-known and can be readily synthesized. For Formula VII compounds in which n=0, either the sodium salt of the appropriate amino acid can be acryloylated, for example, according to K. Huebner, et al, *Makromol. Chem.*, 11, 109 (1970) or, more efficiently, by the method described in U.S. Pat. No. 4,694,103 which involves the one-pot transformation of a ketone into an N-acryloylamino acid. For Formula VII compounds wherein n=1, a useful preparation is the transformation of 3,3-disubstituted acrylic acids as disclosed by D. I. Hoke, et al., *J. Polym. Sci.: Polym. Chem. Ed.*, 10, 3311 (1972).

Insolubilization is a necessary condition for easy removal of the support (e.g., beads) from the system. This is accomplished by inclusion of a monomer which contains a plurality of polymerizable groups and whose participation in a polymerization reaction results in the physical joining of polymer backbones or crosslinking. Crosslinking is also desirable in polymer-supported materials because the mechanical stability is generally substantially enhanced and some degree of control of bead size can be exercized by manipulation of the level of crosslinking, i.e., in general for a given polymerization condition, the greater the amount of crosslinker the smaller the bead size. The degree of crosslinking depends primarily on the intended use of the support material. In all instances the polymers are insoluble in all solvents and possess a molecular weight which is essentially infinite. For many applications requiring fairly high capacities and involving relatively small solute reaction partners which can diffuse into the swollen polymer support, low to moderate degrees of crosslinking are desired. According to D. C. Sherrington, *Br. Polym. J.*, 16, 164 (1984), these crosslinked swellable supports (referred to as "gel-type" polymers) result from inclusion of from 1 to 20 parts of a multifunctional monomer. For certain applications requiring low degrees of physical expansion due to swelling and which can tolerate lower capacities, (as in certain operations conducted in confined flow systems such as chromatographic columns or column reactors), highly crosslinked hydrophobic systems resulting from copolymerization of more than 20 parts of a multifunctional monomer are utilized. These are so-called "macroporous" polymers which are generally regarded as being non-swelling, and solute/support reactions occur primarily at the solvent/support interface. Applications of these supports may involve large solutes, e.g., biomacromolecules, which cannot, because of their large size, diffuse into the polymer network.

In sum, the prior art teaches that in hydrophobic systems 20 parts or more of crosslinker results in a non-swelling system.

We have found with the hydrophilic supports of the present invention, however, that in order to achieve a condition of low swelling in aqueous media, a substantially greater concentration of multifunctional monomer is necessary than the 20 parts commonly utilized in the so-called non-swelling, hydrophobic, macroporous resins described above. This may be a consequence of the utilization of these hydrophilic supports in water and the high degree of hydrophilicity imparted by the multifunctional monomers themselves, as they consist largely of highly polar functional groups.

The prior art generally has taught polymer supports (beads) comprising hydrophobic comonomers and hydrophobic crosslinking monomers in order to achieve crosslinked polymer beads. These were known to be swellable when 1 to 20 parts of crosslinker were present. Above 20 parts of difunctional monomer (crosslinker) provided essentially non-swelling beads. U.S. Pat. No. 4,070,348 teaches that 0.2 to 5 mol % of crosslinking monomer provides beads with a high degree of swelling in water. The patentee believes that this low degree of crosslinking and accompanying high degree of swelling is necessary to achieve high binding capacity.

In the instant invention, hydrophilic comonomers and hydrophilic crosslinkers are utilized. Swelling of beads so produced varies inversely with the amount of multifunctional crosslinker present. Polymer supports (e.g., beads packed together) with a low degree of swelling (less than 3 times the unswelled volume) generally require substantially greater than 20 parts of difunctional crosslinker.

Surprisingly, there can still be a relatively low degree of swelling and high binding capacities of polymer beads in water with more than 5 mol % crosslinker (in hydrophilic systems). Such beads are useful as complexing agents, catalysts, polymeric reagents, chromatographic supports, and enzyme-, other protein-, and other biomacromolecule-bearing supports.

To achieve polymer beads with a low degree of swelling and still maintain high binding capacity, substantially greater amounts of crosslinker are required in hydrophilic systems. Such polymer beads are particularly useful in chromatographic applications and column reactors.

Suitable multifunctional crosslinking monomers include ethylenically unsaturated ($\alpha,\beta$-unsaturated) esters such as ethylene diacrylate, ethylene dimethacrylate, trimethylolpropane triacrylate and trimethacrylate, and $\alpha,\beta$-unsaturated amides, such as methylenebis(acrylamide), methylenebis(methacrylamide), N,N'-diacryloyl-1,2-diaminoethane, N,N'-dimethacryloyl-1,2-diaminoethane, and reaction products of 2-alkenyl azlactones and short chain diamines such as those represented by Formulae VIII and IX:

VIII

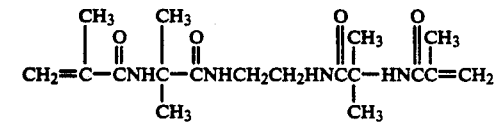

IX

The crosslinking monomers should be at least sparingly soluble in water but need not be as water soluble as defined for the water soluble monomer component. This is not generally a problem for the preparation of gel-type polymers because relatively small proportions of the crosslinking monomers are utilized with relatively large quantities of water solvent, and often the water soluble monomer component, especially N,N-dimethylacrylamide and N-vinylpyrrolidone, will facilitate solution of the crosslinking monomer. For macroporous polymers, however, in which the concentration of crosslinking monomer is greater than 20 parts it may be necessary to add a co-solvent which will facilitate dissolution of the crosslinking monomer. Suitable co-solvents include N,N-dimethylformamide, N,N-dimethylacetamide, N-methylpyrrolidone, and dimethylsulfoxide.

The technique of polymerization employed in the present invention PROCESS I is often referred to as "reverse-phase" or "inverse" suspension polymerization, and a general discussion of this technique is disclosed by M. Munzer, et al., "Suspension Polymerizations from Non-Aqueous Media", in "Polymerization Processes" edited by C. E. Schildknecht and I. Skeist, Wiley-Interscience, New York, pp. 123–124 (1977). The reversal of the normal suspension polymerization technique (in which water is the usual suspending medium) is necessary because the monomers of the present invention are soluble in water and therefore require a water immiscible suspending medium.

The primary purpose of the suspending medium, besides functioning as an inert medium for dispersion of the polymerizable phase, is to dissipate the heat generated in the polymerization reaction. An important characteristic of the suspending medium is its density. In order to obtain spherical polymer beads of uniform size, the beads, once formed, should not exhibit a tendency to sink or float in the suspending medium. Therefore, the suspending medium and aqueous phases should be of approximately the same density.

The actual polymerization occurs in individual droplets of water containing the dissolved monomers and initiator. The droplets are formed and maintained in the suspending medium by vigorous agitation, and the resultant beads' size and individuality (i.e., lack of aggregation) are controlled by the addition of various suspending agents which are surface active molecules that generally contain both hydrophobic and hydrophilic parts.

In and of itself, the polymerization step (step one) is not a novel aspect of the present invention. As is apparent to one skilled in the art, the nature of the suspending medium, the amount of water employed, the initiation system, the amount of crosslinking agent, the stirring rate, and the suspending agent are all essentially independent and important variables that determine the shape and size of the polymeric beads. While not wishing to be bound by any particular set of polymerization conditions, we have found the reverse-phase suspension polymerization procedure described by G. L. Stahl, et al., J. Org. Chem, 44, 3424 (1979) to be exceedingly useful. In that procedure a mixture of heptane and carbon tetrachloride is utilized as the suspending medium; the initiation system is the ammonium persulfate/N,N,N',N'-tetramethyl-1,2-diaminoethane redox couple; the stirring rate is 300 rpm; and the suspending agent is sorbitan sesquioleate. Substitution of the various components by comparable materials can certainly be made, and such substitutions would not be outside the spirit and scope of the present invention. For example, utilizing a polymeric stabilizer such as copoly(i- sooctylacrylate/acrylic acid) or copoly(hexylacrylate/sodium acrylate) instead of sorbitan sesquioleate was found to provide more consistently nonaggregated bead products.

Step two of PROCESS I of the invention consists of conversion of the carboxylate-functional beads into azlactone-functional beads. This is accomplished using a cyclization agent (CA). A cyclization agent is a reagent that can react with the carboxylate-functional beads to form an intermediate adduct which is susceptible to intramolecular attack by the amide carbonyl group to form azlactone groups according to CHEMICAL EQUATIONS IA. This susceptibility is chiefly accomplished by forming a good leaving group (−O(CA) below) for the nucleophilic attack by the carbonyl.

alkyl chloroformates such as methyl, ethyl, and isopropyl chloroformates. Carbodiimides such as N,N'-dicyclohexylcarbodiimide can be effectively utilized but require an additional step of acidifying the carboxylate-functional supports to form carboxyl-functional supports which can then be cyclized to azlactone-functional supports using the carbodiimide reagent. To facilitate understanding of the cyclization step of the invention, the intermediates that would result by employing the aforementioned cyclization agents are depicted below in order of mention.

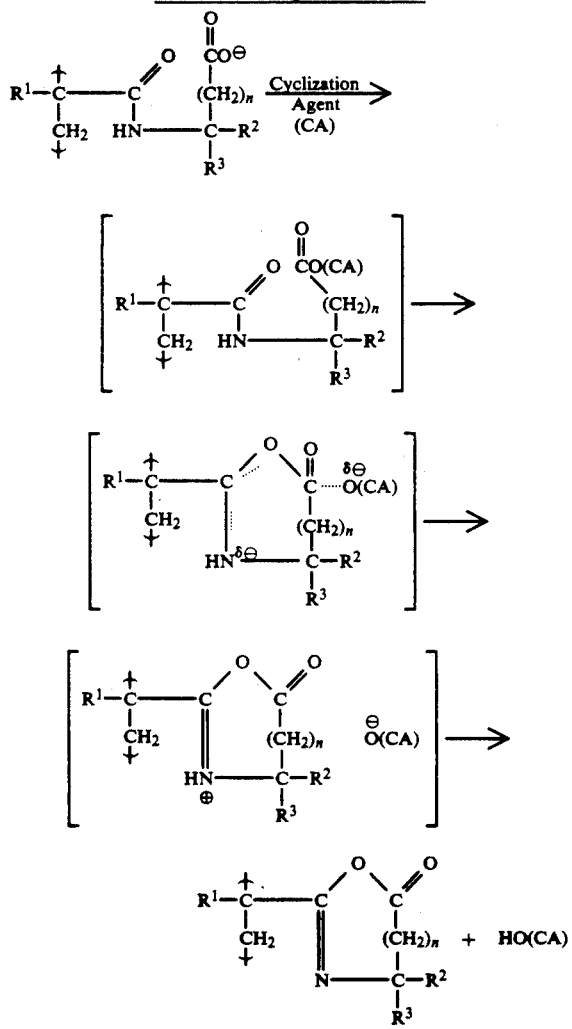

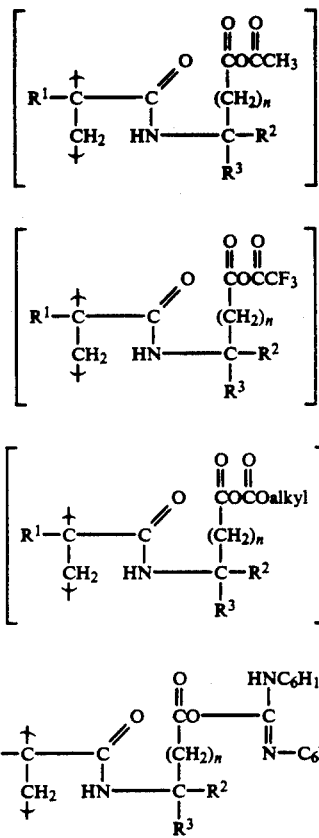

wherein $R^1$, $R^2$, $R^3$, and n are as defined above.

(Structures and formulae depicted between parentheses are partial structures of polymers depicting side chains that actively participate in the cyclization reaction. Use of brackets has the usual meaning of chemical intermediates or activated complexes. Dotted lines mean partial bonds, and δ means partial ionic charges.)

Useful cyclization agents for transformation of the carboxylate-functional supports include, by way of example, acetic anhydride, trifluoroacetic anhydride, and The progress of the cyclization reaction can be easily monitored by examination of the infrared spectrum of the polymer supports. Appearance of a carbonyl stretching absorption at about 1820 cm$^{-1}$ is evidence of azlactone groups. Indeed, one reason azlactone groups are so useful as linkages for covalent attachment to polymers is the ability to monitor reactions by observation of this infrared absorption, either the appearance of it in the synthesis of the azlactone-functional supports or the disappearance of it in the subsequent reaction with a functional material. This absorption is strong, very characteristic of azlactones, and located in a region of the infrared spectrum where essentially no other common absorptions are observed. This is a decided advantage over other linking functional groups such as the chloromethylphenyl and oxirane which lack these unique features in their infrared spectra. A convenient analytical method for monitoring attaching reactions really does not exist with these latter groups.

Because of its low cost, availability, and liquid state at cyclization temperatures, acetic anhydride is a preferred cyclization agent. Typically, the carboxylate-functional supports are covered with acetic anhydride, and the mixture is warmed at temperatures from 40°-100° C., preferably 80°-100° C., for a period of 2-24 hours. After the cyclization reaction, the polymer supports are filtered. What also makes acetic anhydride particularly preferred is that the by-product of cyclization, the alkali metal acetate salt, is fairly soluble inacetic anhydride and can easily be removed from the azlactone-functional supports. The supports can then be dried directly or, as is often conducted, subjected to a series of washing operations with non-reactive organic solvents such as acetone, toluene, ethyl acetate, heptane, and chloroform prior to drying.

PROCESS II

One-Step Reverse Phase Suspension Polymerization

Polymeric supports of PROCESS II of the invention are provided according to the process depicted in CHEMICAL EQUATIONS II, below.

CHEMICAL EQUATIONS II (PROCESS II)

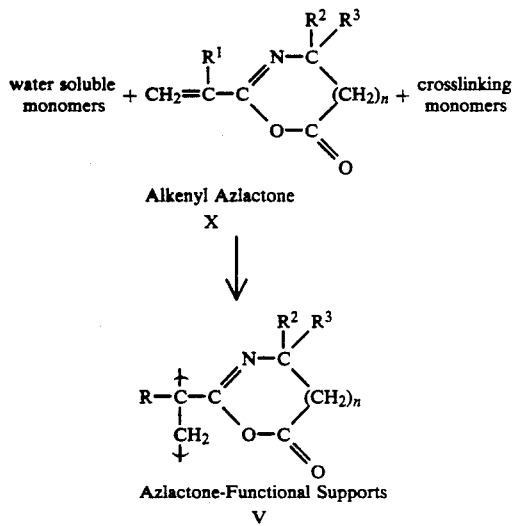

Alkenyl Azlactone
X

Azlactone-Functional Supports
V

This process is conducted by the same polymerization technique as that employed in PROCESS I, and employs the same water soluble monomers and crosslinkers. The major difference is in the utilization of an alkenyl azlactone monomer X instead of the N-acryloylamino acid salt III. The amounts of reactants can be the same as for PROCESS I except that azlactone replaces the salt of N-(meth)acryloylamino acid. This process advantageously provides azlactone-functional polymer supports V in a single step, as opposed to the two-step process of PROCESS 1. Several aspects of this process are surprising in light of the prior art. First of all, the alkenyl azlactones X are fairly soluble in the suspending medium, yet they become readily incorporated in the polymer support (e.g., beads) without detrimental effects upon the polymerization process. (This is in sharp contrast to what is observed employing the teachings of U.S. Pat. No. 4,070,348 (See Examples 47 and 48 below.)) Secondly, the azlactone ring is not hydrolyzed by the water in the aqueous phase during this polymerization process. This is also remarkable considering the teachings of U.S Pat. No. 4,070,348 and of Taylor, supra. After the polymerization process, the beads can be isolated, for example, by filtration, and subjected to a series of washing steps, if desired, and dried.

Useful azlactone monomers and their syntheses are described in U.S. Pat. No. 4,378,411 and in "Polyazlactones", Encyclopedia of Polymer Science and Engineering, Vol. 11, Second Edition, Wiley, N.Y., 1988, pp. 558-571, both of which are incorporated herein by reference, and include:
2-vinyl-4,4-dimethyl-2-oxazolin-5-one,
2-isopropenyl-4,4-dimethyl-2-oxazolin-5-one,
2-vinyl-4,4-diethyl-2-oxazolin-5-one,
2-vinyl-4-ethyl-4-methyl-2-oxazolin-5-one,
2-vinyl-4-dodecyl-4-methyl-2-oxazolin-5-one,
2-vinyl-4,4-pentamethylene-2-oxazolin-5-one,
2-vinyl-4-methyl-4-phenyl-2-oxazolin-5-one,
2-isopropenyl-4-benzyl-4-methyl-2-oxazolin-5-one, and
2-vinyl-4,4-dimethyl-1,3-oxazin-6-one.

Preferred azlactone monomers are
2-vinyl-4,4-dimethyl-2-oxazolin-5-one (which is commercially available from SNPE, Inc., Princeton, N.J.),
2-isopropenyl-4,4-dimethyl-2-oxazolin-5-one, and
2-vinyl-4,4-dimethyl-1,3-oxazin-6-one.

PROCESS III

Dispersion Polymerization

Polymeric supports of PROCESS III of the invention are provided by a polymerization process termed "dispersion polymerization", and in particular, by dispersion polymerization in organic media. In this process which is somewhat analogous to PROCESS II, the monomers and solvent are initially homogeneous. Shortly after polymerization begins, polymer separates as particles and the polymerization then continues in a heterogeneous manner. Polymeric "dispersants" or "stabilizers" are typically used to prevent aggregation of polymer particles during the polymerization process. Techniques for dispersion polymerization in non-aqueous media are well-known in the art, and are described in detail, for example, by K. E. J. Barrett in "Dispersion Polymerization in Organic Media", Wiley, N.Y., 1975. A dispersion polymerization technique which has proven advantageous for the preparation of azlactone-functional supports of the present invention of PROCESS III is that described by Y. Almog, et al., Brit. Polym. J., 1982, 131, which is incorporated herein by reference.

In general, azlactone-functional polymer supports of Formula V are prepared according to PROCESS III by subjecting to a free radical polymerization reaction the following group of monomers:
i) 1-100 molar parts of at least one alkenyl azlactone of Formula X;
ii) 0-99 molar parts of at least one crosslinking monomer; and
iii) 0-99 molar parts of at least one comonomer.

Suitable crosslinking monomers for use in this polymerization process include the ones useful for PROCESSES I and II. However, since water solubility is not a criterion in dispersion polymerization but rather solubility in the dispersing medium, other crosslinkers may be utilized such as, for example, divinyl compounds such as divinylbenzene.

Comonomers useful for the preparation of supports according to PROCESS III include the water soluble comonomers useful in PROCESSES I and II, but again include additional comonomers which are not water soluble. Virtually any free radically polymerizable monomer may be utilized as comonomer subject to the requirement that it have initial solubility in the dispersing medium.

Examples include: the vinyl aromatic monomers such as styrene, α-methylstyrene, 2- and 4-vinylpyridine; α,β-unsaturated carboxylic acids such as acrylic acid, methacrylic acid, itaconic acid, maleic acid, fumaric acid, and crotonic acid; α,β-unsaturated carboxylic acid derivatives such as methyl methacrylate, butyl methacrylate, 2-ethylhexyl methacrylate, ethyl acrylate, butyl acrylate, iso-octyl acrylate, octadecyl acrylate, cyclohexyl acrylate, tetrahydrofurfuryl methacrylate, phenyl acrylate, phenethyl acrylate, benzyl methacrylate, α-cyanoethyl acrylate, maleic anhydride, diethyl itaconate, acrylamide, methacrylonitrile, N,N-dimethylacrylamide, and N-butylacrylamide; vinyl esters of carboxylic acids such as vinyl acetate and vinyl 2-ethylhexanoate; vinyl halides such as vinyl chloride and vinylidene chloride; vinyl alkyl ethers such as methyl vinyl ether, 2-ethylhexyl vinyl ether, and butyl vinyl ether; olefins such as ethylene; N-vinyl compounds such as N-vinylpyrrolidone and N-vinylcarbazole; vinyl ketones such as methyl vinyl ketone; and vinyl aldehydes such as acrolein and methacrolein.

As is well known to one skilled in the art of dispersion polymerization, an inert diluent or dispersing medium must be chosen which will dissolve the monomer or monomer mixture but will precipitate the polymer as it forms. This presents a particular problem when preparing crosslinked polymers, since they are insoluble in all solvents. Therefore a dispersing medium must be chosen which will favor the separation of discrete particles during the polymerization process rather than formation of a crosslinked mass. A useful concept to aid in the determination of dispersing media or in choosing appropriate monomer mixtures which may be dispersion polymerized in a particular medium is the concept of solubility parameter. This concept and its relationship to dispersion polymerization is discussed in detail by Barrett, supra (Chapter 4). Tables of solubility parameter values for many solvents and some polymers, as well as methods for the estimation of solubility parameter values for polymers and copolymers, can be found in *Polymer Handbook*, J. Brandrup and E. H. Immergut, Editors, 2nd Edition, Wiley, New York, 1975, p. IV-337ff. In general, for a successful dispersion polymerization, the solubility parameter of the dispersing medium and of the polymer being formed should differ by at least about 1 to 1.5 solubility parameter units, preferably by 1.5 to 2 or more solubility parameter units. Therefore, for most monomer mixtures, solvents useful as dispersing media include nonpolar hydrocarbons such as pentane, hexane, petroleum ether, cyclohexane, and toluene, and the polar, hydroxylic solvents such as the alcohols methanol, ethanol, isopropanol, and t-butanol.

Initiators useful for PROCESS III of the invention include all free radical initiators which are soluble in the dispersing medium. Choice of the initiator will depend, as is well known in the art, upon the temperature at which the polymerization is conducted. Initiators useful at elevated temperatures, such as at 50° C. or higher, include azo compounds, such as azobisisobutyronitrile, and peroxides or hydroperoxides such as benzoylperoxide, di-t-butylperoxide, t-butylhydroperoxide, and cumene hydroperoxide. For lower temperature reactions, for example at room temperature, redox initiators may be utilized such as, for example, peroxides or hydroperoxides in combination with a tertiary amine. One such redox system is benzoyl peroxide/ N,N-dimethylaniline. Initiators can be present in an amount in the range of 0.1 to 10 weight percent of the monomer composition, preferably 0.5 to 2.0 weight percent.

As mentioned above, the dispersion polymerization procedure of Almog, et al., has been used effectively for the preparation of azlactone-functional supports by PROCESS III. This procedure employs an alcohol as the dispersing medium, and azobisisobutyronitrile as the initiator. A polymeric stabilizer such as polyvinylpyrrolidone, poly(vinyl methyl ether), polyacrylic acid, or polyethyleneimine is used in conjunction with Aliquat 336 (Henkel Corporation) as cosurfactant. Again a surprising and unexpected result of this procedure is that azlactone-functional polymer supports, both crosslinked and noncrosslinked, may be prepared in one step in this hydroxylic medium without reaction of the alcohol solvent with the azlactone. Isolation involves a simple filtration, washing if desired, and drying.

While the beads prepared by the three processes described above all exhibit azlactone functionality on their surfaces, their physical properties may vary widely depending upon the process used for their preparation. The beads prepared via reverse phase suspension polymerizations are generally highly porous (i.e., 10 to 90 volume percent voids, preferably 20 to 75 volume percent voids), with large surface areas and pore volumes, and have a high density of reactive groups. These beads are useful for applications in which binding capacities are of relatively more importance than are reaction kinetics. Beads produced by dispersion polymerizations, on the other hand, are generally smaller in size and are much less porous, in some instances being virtually nonporous. With these beads, reaction kinetics are very fast, a characteristic which can be particularly useful in certain applications such as those requiring higher throughput rates.

PROCESS IV (Coating Solid Supports With Uncrosslinked Azlactone Polymers)

As noted above, polymeric supports of the invention can be in the form of beads. This is a physical form in which the supports possess great utility, particularly for uses such as packing chromatographic columns. However, the new materials are not restricted to the physical form of beads. We have found that certain soluble azlactone polymers (uncrosslinked) can also be coated on a number of substrates and they exhibit the same reactive azlactone functionality in these forms as they do as beads. Thus, these substrates may be used for reaction with functional materials. For example, nylon filtration membranes and glass surfaces can be coated with azlactone polymers of this invention, by dipping the object to be coated into a solution of the polymer and allowing the dipped object to dry. Similarly, particulate material, such as ceramics (e.g., zirconium oxide) or unreactive polymers, such as particles of polyethylene, can be coated with azlactone functional polymers. Other solution coating methods well known in the art may be used, such as for example spray coating and knife coating, depending upon the physical form of the substrate.

Similar results have been obtained when silica beads were used as a substrate upon which azlactone-functional polymers of this invention were coated. This kind of bead is commonly used as a packing in chromatographic columns. Likewise, using glass beads of controlled pore size, again a common column packing medium, significantly improved protein binding and covalent binding have been found when using an azlactone-functional coating. Particular advantages of azlactone-functional supports of PROCESS IV are their incompressibility and almost complete lack of swelling.

The azlactone functional polymers useful for preparing coatings on solid substrates are well known in the art or can be prepared by techniques well known in the art. These polymers are prepared in general by free radical polymerization of one or more alkenyl azlactones, optionally with one or more free radically polymerizable, ethylenically unsaturated comonomers, using polymerization procedures common in the art. Suitable azlactone containing polymers and copolymers are described, for example, in R. Huebner, et al., *Angew. Makromol. Chem.*, 1970, 11, 109 and in U.S. Pat. No. 4,378,411. Particularly suitable azlactone-functional polymers for preparing coatings on solid supports can be prepared by reacting a portion of the azlactone groups of the above azlactone-containing homopolymers or copolymers with a lower alkyl amine or alcohol.

Other methods are available for preparing azlactone-functional supports. One method is to apply alkenyl azlactone monomer to the support (optionally along with other co-monomers) and polymerize the monomer(s) in place. Methods of polymerization include photopolymerization (utilizing an appropriate photoinitiator) as is well known in the art.

The azlactone-functional polymer supports of the invention have now been formed and are ready for reaction with a functional material. As indicated earlier, a surprising discovery was that functional materials can often be attached to azlactone-functional supports of the invention in solvents such as water that have heretofore been thought of as being reactive with azlactones. "Material" as used herein means the principal chemical entity that is desired to be attached to a polymer support to accomplish a specific purpose. Stated another way, "material" means that portion or residue of the "functional material" which actually performs the adsorbing, complexing, catalytic, or reagent end-use. "Functional" for purposes of this invention means that portion of the "functional material" which contains a group that can react with an azlactone. "Functional" groups useful in the present invention include hydroxy, primary amine, secondary amine, and thiol. These groups react, either in the presence or absence of suitable catalysts, with azlactones by nucleophilic addition as depicted in equation (2) below.

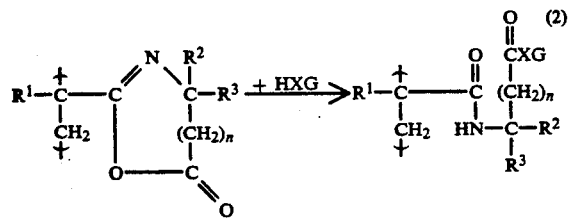

wherein $R^1$, $R^2$, $R^3$, n, X, and G are as previously defined.

Depending on the functional group present in the functional material, catalysts may be required to achieve effective attaching reaction rates. Primary amine functional groups require no catalysts. Acid catalysts such as trifluoroacetic acid, ethanesulfonic acid, toluenesulfonic acid, and the like are effective with hydroxy and secondary amine functional groups. Amine bases such as triethylamine, 1,8-diazabicyclo[5.4.0]undec-7-ene (DBU) and 1,5-diazabicyclo[4.3.0]non-5-ene (DBN) (both available from Aldrich Chemical Co., Milwaukee, Wis.) are effective as well for hydroxy and thiol functional groups. The level of catalyst employed is generally from 1 to 10 parts, preferably 1 to 5 parts, based on 100 parts of azlactone.

As is apparent to one skilled in the art, specific reaction conditions such as solvent, temperature, level of catalyst, etc. vary tremendously depending on the functional material that is to be attached. Because of the myriad of functional materials that have been or could be attached to polymer supports, any listing of functional materials beyond the generic HXG of equation (2) and CHEMICAL EQUATIONS I would be incomplete and somewhat unnecessary, as the inventive aspects of the present invention do not reside with the functional materials. What is -novel is that these functional materials can be covalently bound to azlactone functional supports.

Having described the invention in general terms, objects and advantages of the invention are more specifically illustrated by the following examples. The particular materials and amounts thereof recited in the examples, as well as other conditions and details, should not be construed to unduly limit this invention. In the Examples below numbers in parentheses ( ) are in weight percent, and those in brackets [ ]are in mole percent.

EXAMPLE 1

This example teaches the preparation of an azlactone functional support according to PROCESS I.

Preparation of Copoly(N,N-Dimethylacrylamide: 2-Vinyl-4,4-Dimethylazlactone:Methylenebisacrylamide) (46:46:8) [54.8:39.0:6.1]

Step 1: Preparation of Copoly(N,N-Dimethylacrylamide (DMA): N-Acryloylmethylalanine Sodium Salt (NaAMA):Methylene-bisacrylamide (MBA)) (44.6:50.4:7.8): A two-liter creased, round bottomed flask equipped with a mechanical stirrer (stirring rate about 300 rpm), nitrogen inlet, thermometer, and condenser was charged with heptane (1043 mL) and carbon tetrachloride (565 mL). This solution was stirred and sparged with nitrogen for 15 minutes. A separate solution was prepared consisting of a sodium hydroxide solution (6.6 grams; 0.165 mole dissolved in 85 mL of water), N-acryloylmethylalanine (AMA) (25.98 grams; 0.165 mole), DMA (23 grams; 0.232 mole), MBA (4 grams; 0.026 mole), and ammonium persulfate (1 gram; 0.004 mole) and added to the organic suspending medium. Sorbitan sesquioleate (Arlacel TM 83, ICI Americas, Inc., Wilmington, Del.) (2 mL) was added and the mixture stirred and sparged with nitrogen for 15 minutes. N,N,N',N'-tetramethyl-1,2-diaminoethane (2 mL) was added and the reaction temperature rose fairly quickly from 21° C. to 33° C. The mixture was stirred at room temperature for three hours. The mixture was efficiently filtered using a "D" (greater than 21 micrometers) sintered glass funnel, and the filter cake washed thoroughly and repeatedly with acetone. After drying at 60° C. and less than 1 Torr. for 12 hours, the dry solid (52 grams) was sieved and separated into four fractions: beads less than 38 micrometers, 12.32 grams; beads between 38 and 63 micrometers, 19.83 grams; beads between 63 and 90 micrometers, 4.56 grams; and beads greater than 90 micrometers, 13.95 grams. Employing an optical microscope arrangement consisting of a Nikon Nomarski Differential Interference Contrast Microscope, a Dage Newvicon video camera, a Sony ½" video recorder, and a Perceptive Systems, Inc. digital image processor with accompanying software, it was determined that the 38-63 micrometer sample consisted of quite spherical beads (average aspect ratio=0.87) which swell in water with an accompanying increase in diameter of from 35-50%.

Step 2: Cyclization to Copoly(DMA:2-vinyl-4,4-dimethylazlactone (VDM):MBA) (46:46:8): Acetic anhydride (100 mL) was added to 15.1 grams of the 38-63 micrometer beads prepared in Step 1. The mixture was heated to 100° C. for two hours. After cooling and filtering, the beads were placed in a Soxhlet extraction apparatus and were extracted with ethyl acetate for 16 hours. After drying at 60° C. and less than 1 Torr., the beads weighed 12.6 grams.

EXAMPLE 2

This example teaches use of the reaction product of 1,2-diaminoethane and VDM as a crosslinking monomer (PROCESS I).

Preparation of N,N'-bis(2-acrylamido-2-methyl-propionyl)-1,2-diaminoethane

A 100 mL, three-necked, round bottomed flask equipped with a magnetic stirring bar, a dropping funnel, thermometer, and condenser was charged with VDM (13.9 grams; 0.10 mole) and tetrahydrofuran (50 mL). A solution of 1,2-diaminoethane (3.0 grams; 0.05 mole) in tetrahydrofuran (10 mL) was added dropwise such that the temperature did not exceed 30° C. After stirring overnight the reaction mixture was filtered to remove a white solid which after washing with hexane and drying at less than 1 Torr. weighed 15.8 grams (93% yield). The solid melted at 207°-210° C. and exhibited satisfactory elemental analyses and spectral characteristics for the desired material, which is the compound of Formula VIII in the specification.

Preparation of Copoly(N,N-Dimethylacrylamide:2-Vinyl-4,4-Dimethylazlactone:N,N'-Bis(2-Acrylamido-2-Methyl-Propionyl)-1,2-Diaminoethane) (55:42.7:2.3)

The two-step procedure of Example 1 was utilized except MBA was replaced by the above prepared crosslinking monomer (1.0 gram; 0.003 mole). A sample (15.1 grams) of the intermediate carboxylate-functional polymer was treated with acetic anhydride to yield, after washing and drying, 11.0 grams of the azlactone-functional polymer.

EXAMPLE 3

This example teaches the reaction of a gel-type polymer and a relatively low molecular weight, intrapolymer support-diffusible functional material. The example further teaches a procedure for quantitative determination of azlactone groups.

The procedure is a variation of a quantitative analysis of isocyanates and isothiocyanates using n-butylamine (cf. S. Siggia, "Quantitative Organic Analysis via Functional Groups", John Wiley & Sons: New York, p. 558 (1963)). Generally, the procedure involves treatment of the azlactone-functional beads with standard triethylamine in N,N-dimethylformamide (DMF) to react with and determine the concentration of any uncyclized carboxyl groups. To another sample of beads, excess standard n-butylamine in DMF is added and shaken for 24 hours at room temperature. The excess concentration of n-butylamine is then determined by potentiometric titration with standard acid as an indirect measure of the concentration of azlactone groups. Using this method with the beads of EXAMPLE 2, three separate determinations showed minimal, i.e., less than 0.3 milliequivalents/gram (meq/g) of resin, carboxyl content and an average azlactone content of 2.2 meq/g. Theoretical azlactone content was 3.1 meq/g. Therefore, over 70% of the theoretical azlactone groups had formed and were accessible by the n-butylamine functional material

EXAMPLE 4

This example further teaches the reaction of a gel-type polymer with a relatively small functional material, N-(3-aminopropyl)morpholine, but in an aqueous reaction solvent. Determination of reactable azlactone content is made by measuring the increase in % nitrogen of the reacted beads. This procedure is more time consuming than the quantitative analysis method outlined in EXAMPLE 3, but comparison of the results serves as a check on the accuracy of the titration method.

A gel-type polymer consisting of DMA:VDM:MBA (53.8:41.7:4.5) [62.3:34.4:3.3] was prepared as in EXAMPLE 1; the theoretical % nitrogen present in the beads should be 12.6%; experimentally observed using a Kjeldahl method was 12.1%.

The azlactone-functional beads (1.44 grams; containing approximately 0.004 mole of azlactone groups), N-(3-aminopropyl)morpholine (0.80 gram; 0.0055 mole), and 15 mL of a standard aqueous pH 9 buffer solution were placed in a 100 mL, round bottomed flask and stirred at room temperature. After four hours the beads were filtered, washed repeatedly with deionized water, and dried at 60° C. and less than 1 Torr. The resulting adduct possessed a nitrogen content of 13.8%. Theoretically, the increase in nitrogen should have been 17.4%. The experimentally observed increase of 12.3% again indicates that 70% of the azlactone groups had formed and reacted. This result is in excellent agreement with the titration procedure result of EXAMPLE 3. Furthermore, the result indicates that measurable hydrolysis in the aqueous pH 9 buffer solution did not occur and that virtually quantitative attaching reactions can take place in aqueous media at an elevated pH.

EXAMPLES 5-7

These examples illustrate how polymer bead size can be controlled by the level of crosslinking monomer (PROCESS I).

The procedure of Step 1 of EXAMPLE 1 was utilized to prepare the carboxylate-functional beads of the following examples as shown in TABLE I, below. Average particle diameters were determined using an optical microscope equipped with a Zeiss IBAS ™ Image Analyzer. It is apparent that as the level of crosslinker increases the particle diameter decreases.

TABLE I

| EXAM-PLE | Monomer wts. (g) [mole %] | | | Wt % cross-linker | Average particle diameter (micrometers) |
|---|---|---|---|---|---|
| | DMA | NaAMA | MBA | | |
| 5 | 24 | 24 [62.2:34.4:3.3] | 2 | 4 | 67.5 |
| 6 | 23 | 23 [60.7:33.5:6.8] | 4 | 8 | 42.2 |
| 7 | 21 | 21 | 8 | 16 | 32.4 |

TABLE I-continued

| EXAMPLE | Monomer wts. (g) [mole %] | | | Wt % cross-linker | Average particle diameter (micrometers) |
|---|---|---|---|---|---|
| | DMA | NaAMA | MBA | | |
| | [55.6:30.7:13.6] | | | | |

EXAMPLES 8-10

These examples teach the preparation of highly crosslinked polymers of the invention (PROCESS I). They furthermore teach utilization of a co-solvent to facilitate dissolution of the crosslinking monomer.

The method of EXAMPLE 1 was utilized except the monomers and initiator were dissolved in water (75 grams) and DMF (30 grams). The azlactone content was determined utilizing the titration procedure of EXAMPLE 3, and is shown in TABLE II, below.

TABLE II

| EX. | Monomer wts. (g) [mole %] | | | Average particle diameter (micrometers) | Azlactone content (meq/g) | |
|---|---|---|---|---|---|---|
| | DMA | NaAMA | MBA | | theoretical | measured |
| 8 | 34.02 | 4.48 | 12.5 | 26.0 | 0.5 | 0.29 |
| | [76.4:5.5:18.0] | | | | | |
| 9 | 30.55 | 8.95 | 12.5 | 20.5 | 1.0 | 0.52 |
| | [70.1:11.4:18.4] | | | | | |
| 10 | 27.08 | 13.42 | 12.5 | 25.0 | 1.5 | 1.10 |
| | [63.6:17.4:18.9] | | | | | |

The polymer beads prepared in Examples 8 to 10 can be reacted with a functional material to provide a chromatographic support, a complexing agent, a polymeric reagent, or a catalyst.

EXAMPLE 11

This example teaches the preparation of a polymer with N-methacryloylmethylalanine sodium salt (NaMMA) instead of NaAMA (PROCESS I). The resulting azlactone-functional bead of Formula V was formed with $R^1=CH_3$.

The procedure of EXAMPLE 9 was utilized except that NaMMA (9.65 grams) was substituted for the NaAMA. The resulting azlactone-functional beads which were formed after treatment with acetic anhydride had an average particle diameter of 22.4 micrometers and an azlactone functionality of 0.68 meq/g.

EXAMPLE 12

This example teaches the preparation of a polymer with N-vinylpyrrolidone as the water soluble monomer component (PROCESS I). The procedure and monomer charges of EXAMPLE 9 were utilized except the DMA was replaced by N-vinylpyrrolidone. The average particle diameter of the beads resulting from Step 1 was 19.3 micrometers Cyclization afforded azlactone-functional beads which possessed a strong azlactone carbonyl absorption band at about 1820 $cm^{-1}$ in the infrared.

EXAMPLE 13

This example teaches the synthesis of a six-membered ring azlactone (2-oxazin-6-one) functional polymer bead (PROCESS I).

The procedure of EXAMPLE 9 was utilized except 3-acrylamido-3-methylbutyric acid sodium salt (9.65 grams) was utilized instead of NaAMA After cyclization the 2-oxazin-6-one functional beads possessed an average diameter of 28.5 micrometers and a functional level of 0.16 meq/g.

EXAMPLE 14

This example teaches the reaction of an azlactone-functional polymer bead with a protein functional material.

Preparation of Radiolabeled Protein A

Protein A (2.5 mg) (from *Staphylococcus aureus*) (Genzyme Corp., Boston, Mass.) was dissolved in 10 mM potassium phosphate buffer (pH 7.0; 0.6 mL) and two Iodo-beads TM (an insoluble form of chloramine T; Pierce Chemical Co., Rockford, Ill.) were added to catalyze the addition of iodine to tyrosine residues. The reaction was initiated by the addition of 0.1 milli Curies (mCi) of NaI (carrier-free $^{125}I$, New England Nuclear Co., N. Billerica, Mass.). The reaction was incubated at 20° C. for 30 minutes with vigorous manual shaking at five minute intervals. Protein A (both iodinated and unmodified forms) was separated from NaI by elution through a Pharmacia PD-10 size exclusion column in the same phosphate buffer. The fractions which contained protein were combined, aliquotted, and frozen at $-15°$ C. until used. Specific radioactivity on day 0 was 154,000 counts per minute (cpm)/$\mu$g. All subsequent calculations were corrected for the radioactive half-life of $^{125}I$ of 60 days. Radioactive Protein A was not used beyond six weeks after iodination.

Reaction of the Radiolabeled Protein A with an Azlactone-Functional Bead

The azlactone-functional polymer utilized was that prepared in EXAMPLE 5. The polymer beads (0.010 gram) were placed in a centrifuge tube and were covered with a solution consisting of the labeled Protein A preparation above (100 $\mu$L) and 400 $\mu$L of a phosphate buffer solution (pH 7.5). The mixture was shaken gently at room temperature for 90 minutes. The tube was centrifuged, and the original supernatant and five successive washes (1 mL of pH 7.5 buffer) were collected and their $^{125}I$ content determined using a Packard Auto-Gamma Scintillation Spectrometer Model 5230. The original supernatant exhibited 42,415 cpm (above background); first wash: 6722; second wash: 836; third wash: 202; fourth wash: 48; and fifth wash: 18 cpm. Ethanolamine (400 microliters of 0.5M in pH 7.5 phosphate buffer) was added and shaken with the beads for 90 minutes to react with all the remaining azlactone residues. Finally, after an additional four washes with buffer solution the beads and the reaction vessel were counted and exhibited 7002 and 1865 cpm, respectively. This correlates to a level of 2.54 micrograms of Protein A/10 mg of beads.

A CONTROL experiment was conducted in the same manner except the order of addition of Protein A and ethanolamine was reversed. The CONTROL exhibited a level of 0.14 microgram of Protein A/10 mg of beads.

In a similar fashion, the effects of the catalyst DBU were examined, with the DBU (25 microliters) being added to the initial Protein A buffer solution The result was a level of 3.90 micrograms of Protein A/10 mg of beads.

EXAMPLE 15

This example illustrates that the Protein A is not just adsorbed or adhering to the beads in some fashion but is actually covalently bound to the polymer beads. The amount of covalently bound protein may be estimated by determining the amount of protein resistant to sodium dodecylsulfate (SDS) treatment. SDS denatures protein so that only those molecules which are covalently bound will remain attached to the beads.

In this experiment, the polymer beads (10 mg) of EXAMPLE 14 (having 3.90 micrograms Protein A/10 mg of beads) were incubated with 1% sodium dodecylsulfate (SDS) (500 microliters) at 37° C. for two hours, followed by centrifugation, and five buffer (550 microliters; pH 7.5) washes. Analysis of the radioactivity of the beads revealed that 73% of the protein remained attached to the beads.

EXAMPLE 16

This example illustrates that the Protein A attached to the polymer beads remains active and is not denatured in the attaching process.

Biologically active Protein A can be assayed by determining the amount of antibody which it can bind. Antibody (IgG) conjugated with an enzyme marker, alkaline phosphatase was purchased from Cooper Biomedical (Malvern, Pa.).

In this experiment, 1.0 mg of the polymer beads of EXAMPLE 5 were reacted with unlabeled Protein A and ethanolamine as described in EXAMPLE 14. The beads were reacted with the enzyme-antibody conjugate for 2 hours. After centrifugation and washing steps, Protein A and CONTROL beads were resuspended in the alkaline phosphatase assay solution (0.1M sodium glycinate, 1.0 mM $ZnCl_2$, 1.0 mM $CaCl_2$, 6.0 mM p-nitrophenyl phosphate, pH 10.4) and rocked continuously to promote mixing. Every 10 min the absorbance of the supernatant solution was determined at 405 nm. The absorbance of the TEST beads increased linearly at 5 to 15 times the CONTROL rate, depending on the amount of immobilized Protein A. This showed that the protein remained active.

EXAMPLE 17

This example teaches that the attaching reaction with a protein in aqueous media is rapid.

The beads of Example 6 were reacted with radiolabeled Protein A as described in Example 14 except that the quenching and washing steps were initiated at various times from 5-180 min. The "zero time" was prepared by addition of the quencher ethanolamine first. The reaction was performed in pH 8.5, 20 mM sodium pyrophosphate buffer with DBU. It was observed that at 5 minutes 1.34 micrograms of Protein A/10 mg of beads were bound. This was 80% by weight of the amount bound at 180 minutes.

EXAMPLE 18

This example teaches that a substantially greater concentration of multifunctional monomers is required to achieve a low degree of swelling with hydrophilic polymer beads than with typical hydrophobic macroporous polymer beads which are essentially non-swelling with difunctional monomer concentrations of greater than 20 weight percent.

Employing the procedure of Example 1 with the modification of using 60 mL of DMF cosolvent in step 1, two bead formulations were prepared: DMA:-PIP:VDM (42:16:42) [52.5:10.1:37.4] and MBA:-PIP:VDM (42:16:42) [41.6:12.5:46.0], in which PIP represents N,N'-bis(acryloyl)piperazine prepared by the method of M. C. Tanzi, et al., *Biomaterials*, 5, 357 (1984). In the first set of beads the difunctional monomer molar concentration was 10.1% and in the second set 54%. In graduated cylinders, 0.5 mL (dry volume) of the beads of each set were covered with the pH 7.5 buffer solution. Within 20 minutes, the beads containing 10.1% difunctional monomer had swelled to 3 mL or six times its dry volume, whereas the 54% crosslinked beads had swelled to 1 mL or only twice its dry volume.

Because of their low degree of swelling these beads are especially useful for the preparation of chromatographic supports.

EXAMPLE 19

This example teaches that exceptionally high binding capacities can be achieved with highly crosslinked, azlactone-functional beads and, further, that a surprisingly non-linear relationship exists between capacity and azlactone content (i.e., in certain ranges, a modest increase in reactive group functionality results in an enormous increase in binding capacity).

Two bead formulations were prepared as in Example 18 consisting of MBA:PIP:VDM:DMA (42:16:10:32) [36.4:10.9:9.6:43.1] and MBA:PIP:VDM:DMA (42:16:30:12) [39.4:11.8:31.2:17.5]. These preparations along with the MBA:PIP:VDM (42:16:42) [41.6:12.5:46.0] beads of Example 18 contain relatively high levels, i.e., 47-54%, of difunctional monomers. The three azlactone-functional beads were challenged with radiolabeled Protein A (125 mg/g of beads). Similarly treated was a commercial, oxirane-functional bead preparation, Eupergit-C ™ (available from Rohm Pharma, Weiterstadt, West Germany). (Eupergit-C is believed to be a water swellable, crosslinked polymer bead protected by U.S. Pat. No. 4,070,348.) After washing as in Example 14, the levels of bound Protein A were observed with the various bead preparations as shown in TABLE III, below.

TABLE III

| Bead Sample | [Reactive Group] (meq/g) | Bound Protein A* (mg/g) |
|---|---|---|
| MBA:PIP:VDM:DMA (42:16:10:32 [36.4:10.9:9.6:43.1] | 0.72 | 3.6 |
| MBA:PIP:VDM:DMA (42:16:30:12) [39.4:11.8:31.2:17.5] | 2.15 | 11.3 |
| MBA:PIP:VDM (42:16:42) [41.6:12.5:46.0] | 3.02 | 54.4 |
| EUPERGIT-C | 0.8-1.0** | 9.6 |

*All bound Protein A amounts were greater than 95% SDS resistant.
**According to information provided by the vendor.

It was surprising to note that an increase of 40% in reactive group functionality form the 30 wt % VDM to the 42 wt % VDM was accompanied by an enormous 380% increase in weight of bound protein. The water swellable Eupergit-C product even when projected at equivalent reactive group concentration would bind only from 30-36 ml of Protein A per gram of polymer bead.

EXAMPLE 20

This example teaches that the highly crosslinked, azlactone-functional beads can bind considerably more protein than oxirane beads.

MBA:PIP:VDM (42:16:42) [41.6:12.5:46.0] beads of Example 18 and Eupergit-C ™ beads were reacted with 20–500 mg of radiolabeled Protein A per gram of bead. After washing as described in Example 14, the amounts of bound protein were determined. These results were plotted by a method originally described by Klotz (I. M. Klotz, in "The Proteins", eds. H. Neurath and K. Bailey, Academic Press, Vol. 2, p. 727, 1958) in which the inverse of the Protein A bound is plotted versus the inverse of the Protein A concentration. This method is useful for determining the maximum capacity of a binding group for a ligand by extrapolation to infinite ligand concentration. The maximum binding capacity of Eupergit-C ™ for Protein A was 13.5 mg/gram of bead, much lower than the 245 mg/gram maximum binding capacity of VDM-containing bead. Additionally, SDS treatment as described in Example 15 reveals that 87% of the Eupergit-C ™ Protein A was covalently attached compared with 96% of the VDM Protein A.

EXAMPLE 21

This example teaches that azlactone-functional beads can perform well as a stationary phase in high performance (pressure) liquid chromatography (HPLC).

Eupergit-C ™ and MBA:PIP:VDM (42:16:42) [41.6:12.5:46.0] of Example 18 were each packed into identical 3×50 mm glass HPLC columns and subjected to a regimen of increasing flow rates using a Pharmacia FPLC liquid chromatography pumping system. At a flow rate of 1 mL/min the back pressures observed were 1.0 megapascal (MPa) (Eupergit-C ™) and 0.8 MPa (azlactone), and at 2.5 mL/min the pressures were 1.6 and 1.3 MPa, respectively. Neither column bed appeared compressed during the lengthy testing period.

EXAMPLE 22

This example teaches that a column of Protein A immobilized onto azlactone-functional beads can function as an affinity column for Immunoglobulin G (IgG) in a high flow system such as might be useful in treatment of a cancer patient.

Protein A was immobilized onto the MBA:PIP:VDM (42:16:42) [41.6:12.5:46.0] beads of Example 18 as described in Example 13, and a 3×37 mm HPLC column was prepared and equilibrated at pH 7.5 in 25 mM sodium phosphate buffer Human blood serum (0.5 mL), diluted 10-fold with buffer, was injected into the column at 0.5 mL/min (2 column volumes/min). After 8 column volumes the column was washed with 1.0M NaCl in the phosphate buffer to remove any non-specifically bound protein Finally, the column was eluted with 1.0M sodium glycinate buffer, pH 3.0, to remove the bound IgG. 200 µg of IgG eluted from the column which yields a useful capacity of 0.6 moles of IgG bound per mole of Protein A immobilized to azlactone-functional beads.

EXAMPLE 23

This example teaches the preparation of a highly crosslinked bead polymer of the invention by the reverse phase suspension polymerization method using monomeric 2-vinyl-4,4-dimethylazlactone instead of its precursor (PROCESS II). Preparation of Copoly(Methylenebisacrylamide:2-Vinyl-4,4-dimethylazlactone) (58:42) [55.5:44.5]

A 3-liter creased, round bottomed flask equipped with a mechanical stirrer (stirring rate 300 rpm), nitrogen inlet, thermometer, and condenser was charged with heptane (1043 mL) and carbon tetrachloride (565 mL). This solution was stirred and sparged with nitrogen for 15 minutes. A separate solution was prepared as follows: Methylenebisacrylamide (29 grams, 0.188 mole) was dissolved in dimethylformamide (160 mL); after solution was achieved, water (160 mL) was added and the resulting solution sparged with nitrogen for 15 minutes. Sorbitan sesquioleate (3 mL) was added and sparging continued for an additional 5 minutes. At this point, ammonium persulfate (1 gram) was added and sparging continued for 1 minute more. The solution was then quickly added to the organic suspending medium. Immediately following this addition, VDM (21 grams, 0.151 mole) was added and the, whole mixture was sparged for an additional 5 minutes. N,N,N',N'-tetramethyl-1,2-diaminoethane (2 mL) was added and the reaction temperature rose fairly rapidly from 22 to 29 degrees C. The reaction mixture was stirred for a total of 4 hours from the time of the diamine addition, then filtered using a "D" (greater than 21 micrometers) sintered glass funnel. The filter cake was washed on the filter with acetone (2×500 mL), then dried at 60 degrees C. and less than torr for 24 hours. IR analysis indicated a strong azlactone carbonyl absorption.

EXAMPLE 24A

A reverse phase suspension polymerization (PROCESS II) was conducted by a procedure similar to that of Example 23 except that a polymeric stabilizer was employed instead of the sorbitan sesquioleate. The polymeric stabilizer was prepared as follows: A solution of copoly(isooctylacrylate:VDM) (95:5) (31.68 grams of a 38.7% solids solution in ethyl acetate) was diluted with acetone (20.54 grams). To this solution was added choline salicylate (1.06 grams, 0.0044 mole) and 1,8-diazabicyclo[5.4.0]undec-7-ene (DBU) (0.1 gram) and the resultant mixture was heated at 55 degrees C. for 15 hours. IR analysis indicated the formation of the desired reaction product.

In the preparation of the bead polymer, 6.0 grams of the above polymeric stabilizer solution was utilized. After conducting the polymerization as described in Example 23, isolating and drying the bead polymer, IR analysis indicated that azlactone groups had all been hydrolyzed. Cyclization was accomplished using acetic anhydride as in Step 2 of Example 1. The beads were then filtered, washed with ethyl acetate (2×500 mL) and diethyl ether (1×500 mL), then dried under pump vacuum (<1 torr) for 24 hours at 65 degrees C.

EXAMPLE 24B

A reverse phase suspension polymerization was conducted by a procedure similar to that of Example 24A except that the polymeric stabilizer used was copoly(isooctylacrylate:N-acryloylmethylalanine, sodium salt) (90.5:9.5). IR analysis of the beads obtained indicated that no hydrolysis of the azlactone ring had occurred during the polymerization.

EXAMPLES 24C, 24D, AND 24E

Reverse phase suspension polymerizations were conducted by the procedure of Example 24A except that the polymeric stabilizer used was (24C) 90:10 copoly(isooctylacrylate: acrylic acid, sodium salt), (24D) (90:10) copoly(isooctylacrylate: acrylic acid), and (24E) (91.8:8.2) copoly(isooctylacrylate: N-acryloyl-α-aminoisobutyramide).

In all cases, IR analysis of the beads obtained indicated that no hydrolysis of the azlactone ring had occurred during polymerization.

EXAMPLE 25A

The following examples teach preparation of azlactone-functional bead polymers by dispersion polymerization in alcoholic media (PROCESS III).

Preparation of Copoly(2-Vinyl-4,4-dimethylazlactone: Ethyleneglycol Dimethylacrylate) (42:58)

A 1-liter creased, round bottomed flask equipped as in Example 23 was charged with t-butyl alcohol (400 mL), polyvinylpyrrolidone (7.0 grams), and Aliquat ™ 336 (2.0 grams) (available from Henkel Corp., Kankakee, Ill.). VDM (21 grams), ethyleneglycol dimethacrylate (EGDMA, 29 grams), and azobis(isobutyronitrile) (AIBN) (0.5 gram) were mixed, and the resultant solution added to the reaction vessel. Nitrogen gas was bubbled through the stirred reaction mixture for ten minutes, then the flask was immersed in an oil bath preequilibrated to 70 degrees C. Stirring and heating was continued for 2.5 hours, then the mixture was allowed to cool and was filtered. The filter cake was washed two times with acetone and dried at 50 degrees C. in a circulating air oven to give 43 grams of colorless polymer beads. IR analysis showed the azlactone ring to be intact, and that no apparent reaction with the alcohol solvent had taken place.

Additional examples of polymer beads were prepared by procedures similar to those described in this example except that different dispersing solvents, different monomer ratios, or different comonomers, were utilized. Beads were separately prepared using isopropanol, ethanol, and methanol as the dispersing solvent and methylmethacrylate, hydroxyethyl methacrylate, and 2-isopropenyl-4,4-dimethylazlactone were used as monomers. In all cases, IR analysis indicated that the azlactone ring was intact in the product beads. Table IV shows the various formulations prepared by this method.

TABLE IV

Polymer Beads Prepared By Dispersion Polymerization

| Example | Monomer Composition (wt %) | | | Solvent |
|---|---|---|---|---|
| | VDM | EGDMA | Other | |
| 25A | 48 | 52 | — | t-butanol |
| 25B | 100 | — | — | i-propanol |
| 25C | 10 | 90 | — | i-propanol |
| 25D | 20 | 80 | — | i-propanol |
| 25E | 30 | 70 | — | i-propanol |
| 25F | 60 | 40 | — | i-propanol |
| 25G | 80 | 20 | — | i-propanol |
| 25H | 90 | 10 | — | i-propanol |
| 25I | 42 | 20 | 38 (MMA)a | i-propanol |
| 25J | 40 | 50 | 10 (HEMA)b | i-propanol |
| 25K | 100 (IDM)c | — | — | i-propanol | a = methyl methacrylate.
b = 2-hydroxyethyl methacrylate
c = 2-isopropenyl-4,4-dimethylazlactone

EXAMPLE 26

Polymeric beads from the previous preparations were evaluated for their ability to bind Protein A using labeled protein. Radioiodinated Protein A (Example 14) was diluted with unlabeled Protein A to give a target specific radioactivity of 2000 cpm/µg of protein dissolved in phosphate buffered saline (PBS) 25 mM sodium phosphate, 150 mM NaCl buffer, pH 7.5, with a final protein concentration of g/mL. In triplicate samples 200 µL of Protein A solution was added to 10 mg of beads and allowed to react at room temperature for one hour. The reaction was terminated by removal of the protein solution and addition of 500 µL of 3.0M ethanolamine, pH 9.0, for quenching the unreacted azlactone sites. After 30 minutes, the beads were washed three times with 500 µL of PBS, transferred to clean test tubes, and monitored for bound radioactive protein as in EXAMPLE 14. The following day, the beads were incubated with 500 µL of 1% SDS (sodium dodecylsulfate) in PBS for 4 hours at 37 degrees C. to remove non-covalently bound protein. After incubation, the beads were rinsed three times with 500 µL SDS, and the remaining radioactivity was determined. The data from those experiments is shown in TABLE V, below.

TABLE V

Properties of Azlactone Polymeric Beads

| Bead (Example #) | Protein A binding (mg/g) | SDS resistance (%) |
|---|---|---|
| 23 | 3.2 | 81 |
| 24A | 2.8 | 90 |
| 25A | 1.1 | 96 |
| 25E | 4.1 | 96 |

The data of TABLE V show that beads prepared by PROCESSES II and III exhibited high protein binding capacities similar to those obtained in PROCESS I.

EXAMPLE 27

The surface area and pore size of azlactone polymer beads prepared by the methods of Examples 18, 23, and 25A were measured by standard methods, BET-method (isothermal nitrogen absorption) and mercury porosimetry, respectively. Reactive groups were determined by modifying the method of Example 3 such that the beads were reacted in 0.1M NaOH overnight before titration with standard acid solution. The results, shown in Table VI, indicate that beads prepared by the methods of Examples 18 and 23 produce materials which were significantly more porous than Eupergit-C (values from vendor's information) while the beads produced by the method of Example 25A were nearly nonporous.

TABLE VI

Properties of Polymeric Beads

| Bead | Surface area ($m^2/g$) | Ave. Pore size (Å) | Reactive groups (meq/g) | Reactive density ($\mu eq/m^2$) |
|---|---|---|---|---|
| Ex. 18 | 275 | 650 | 3.02 | 11 |
| Ex. 23 | 200 | 550 | 2.79 | 14 |
| Ex. 25A | 2.85 | 25000 (2.5 µm) | 0.19 | 67 |
| Eupergit-C | 183 | 350 | 0.8–1.0 | 5.5 |

The measured average pore size of the porous azlactone beads of Example 18 and 23 were somewhat larger than Eupergit-C. The large measured pore size (2.5 micrometers) of the azlactone beads of Example 25A is believed to represent the interstitial volume between beads and indicates a lack of a porous structure. The number of reactive groups available on porous azlactone beads was higher than that available on Eupergit-C which could be of great utility when used for chromatographic purposes. When compared as reactive groups per unit area, the nonporous azlactone beads and porous beads were clearly superior to Eupergit-C.

EXAMPLE 28

This example demonstrates the preparation of azlactone-functional polymers which have enhanced coating properties for organic and inorganic substrates (PROCESS IV).

A homopolymer of VDM was prepared by free radical polymerization of the monomer using 2,2'-azobisisobutyronitrile (AIBN) as initiator at 30% solids in methyl ethyl ketone (MEK). Samples of this polymer solution were reacted with methanol using DBU (2-5 mole % based on methanol charged) as catalyst. The amount of methanol used was chosen so as to leave a certain fraction of the azlactone rings of the polymer intact. The homopolymer and five modified polymers with 100, 80, 60, 40, 20, and 0 molar % remaining were prepared. These will be referred to as VDM-100, VDM-80, VDM-60, VDM-40, VDM-20, and VDM-0, respectively, in succeeding examples.

Similarly ethylamine was reacted with a fraction of the homopolymer solution to produce a 60% ethylamide/40% azlactone polymer (VDM-60N).

EXAMPLE 29

This example shows the superior coating properties of modified poly VDM (PROCESS IV).

Glass microscope slides (2.5×7.6 cm); SurgiPath TM ) were dipped three times in a 10% solution of VDM-60 or VDM-100 (Example 28) in ethyl acetate and allowed to air dry for one hour at room temperature (PROCESS IV). The slides were then immersed in distilled water for 5 to 15 minutes and observed for remaining VDM coating. After rinsing, slides coated with VDM-60 polymer showed evidence of the undisturbed VDM polymer coating by the appearance of a faint opalescent sheen. A polymer film was observed to float off the surface of those slides coated with VDM-100. This indicates that the partially methanol reacted azlactone polymer binds substantially better to a glass surface than the unreacted polymer. Similarly glass slides were dip coated in 10% solutions of VDM-100 and VDM-60N and air dried. Pairs of slides were immersed for 10 and 40 minutes in 0.1M HCl solution The VDM-100 coating bubbled and lifted in each case while the VDM-60N coating remained attached and unchanged by the treatment.

To confirm these qualitative observations, sections of plain glass microhematocrit capillary tubing (American Scientific Products, McGaw Park, Ill.) were coated with VDM-60 (Example 28) and allowed to air dry (1.2mm internal diameter, 6 mm length; 2 sections per assay 0.90 cm² total surface area). These samples (in triplicate) were incubated with radioiodinated Protein A as previously described (Example 26). The results (see Table VII, below) show that azlactone-functional polymer coating of the glass increased both the amount of covalently bound protein (17-fold greater than non-treated glass) and the % SDS resistance (4.5-fold increase). In addition, incubation in the aqueous PBS solution at room temperature for 16 hours resulted in no significant loss of bound protein, indicating minimal dissolution of the azlactone-functional polymer coating by aqueous solution over this extended time interval.

TABLE VII

The Binding of Protein A to VDM-60 Coated Glass

| Treatment | Covalently bound protein (ng/cm²) | SDS resistance (%) |
| --- | --- | --- |
| none | 11 | 16 |
| solvent | 26 | 23 |
| VDM-60 | 194 | 72 |

EXAMPLE 30

This example illustrates the coating of silica gel with azlactone-functional polymer and the ability of the coated product to covalently bind protein (PROCESS IV). Chromatographic grade silica beads (Silicar CC-4 TM , Mallinkrodt Chemical, St. Louis, Mo.) were dried in an oven at degrees C., <1 torr, for 24 hours. A sample of this silica gel (9.81 g) was mixed with a 30% solids solution of VDM-100 polymer from Example 28 in MEK (1.63 g). This mixture was covered with more MEK (50 mL) and allowed to stand at room temperature for 3 hours with occasional swirling. The solvent was then removed under reduced pressure and the coated silica gel, now containing 5% by weight azlactone polymer, was dried at <1 torr at room temperature overnight. Similarly VDM-80, VDM-60, VDM-40, VDM-20, and VDM-0 were coated onto silica gel. Approximately mg of each coated silica gel and untreated silica gel were exposed to labeled Protein A and evaluated for protein binding as in Example 26.

The results of radioactivity monitoring of the protein-treated beads and subsequent SDS treatment are shown below in TABLE VIII.

TABLE VIII

The Binding of Protein A to Azlactone-Functional Polymer-Coated Silica Beads

| Bead Type | Bound Protein A (mg/g) | SDS Resistance (%) |
| --- | --- | --- |
| Untreated Silica | 0.15 | 42 |
| VDM-0 | 0.14 | 41 |
| VDM-20 | 1.97 | 94 |
| VDM-40 | 2.44 | 97 |
| VDM-60 | 2.60 | 98 |
| VDM-80 | 2.64 | 98 |
| VDM-100 | 2.50 | 97 |

The data of TABLE VIII show coating the beads with polymer containing 20% residual azlactone (VDM-20) resulted in a 14-fold increase in the amount of protein bound, with SDS resistance more than doubling. Solutions of polymer containing 40% azlactone functionality or higher yielded protein binding at a 17-fold increase over the uncoated silica. The SDS resistance increased to 98% as a result of the azlactone-functional polymer coating on this inorganic support material.

EXAMPLE 31

This example illustrates the ability of partially reaction azlactone polymer to coat zirconium oxide ceramic beads (PROCESS IV).

Zirconium oxide ceramic beads (12.65 g) prepared as described in M. P. Rigney, Ph.D. Thesis, "The Development of Porous Zirconia as a Support for Reverse Phase High Performance Liquid Chromatography", University of Minnesota, Minneapolis, Minn. (1988) were coated as in Example 30 with VDM-60 to a final 5 weight % loading. Coated and uncoated beads were evaluated for protein binding using radioiodinated Protein A.

Approximately 20 mg of each bead type (in triplicate) were incubated with 400 µL of a dilute solution of labeled Protein A (specific radioactivity at 2000 cpm/µg; 250 µg protein/mL) for one hour, at which time 800 µL of 3.0M ethanolamine, pH 9.0, was added to the reaction mixture. After centrifugation and removal of the supernatant, an additional 800 µL of quenching amine was incubated with the beads for 30 minutes. This quench was followed by 3×800 µL rinses with PBS. The beads were then monitored for radioactivity (10 minutes per tube), and were subjected to 1% SDS treatment on the following day (see Example 26).

Azlactone-functional polymer coating of the beads resulted in a 24-fold increase in protein bound to the ceramic material, 0.72 µg protein per mg beads versus 0.03 µg per mg for uncoated beads. In addition, the bound protein was greater than 99% resistant to SDS treatment, indicating covalent bond linkage of the protein to the azlactone-functional polymer-coated zirconium oxide support.

EXAMPLE 32

This example illustrates the preparation of a nylon membrane coated with polyazlactone and the binding of protein to it (PROCESS IV).

Small disks of nylon filtration membrane (Filter-Pure ™ 5 Nylon-66, 0.2 µm; Pierce, Rockford, Ill.) were cut (¼" diameter; total surface area of 0.61 cm$^2$/disk) and immersed in a 1% solution of VDM-60 (Example 28) in ethyl acetate for one hour at room temperature, followed by air drying. Protein A binding was evaluated by the procedure of Example 26 with exception that polyazlactone-coated disk and untreated disks (in triplicate) were treated with 250 µL of labeled Protein A solution and allowed to react at room temperature for one hour, with the initial 30-minute incubation performed under vacuum to ensure complete wetting of the membrane. The reaction was terminated by removal of the protein solution and addition of 500 µL of 3.0M ethanolamine, pH 9.0, for quenching the unreacted azlactone sites as before.

The VDM-60 treated nylon membrane disks showed a 60% increase in covalently bound protein over the untreated disks (757 ng Protein A/cm$^2$ vs. 472 ng/cm$^2$), with a significant six-fold increase in the % SDS resistance (71% compared to 11%). These results indicate that protein binding to this membrane could be increased by a simple treatment with the azlactone-functional polymer.

EXAMPLE 33

This example demonstrates the coating of polyethylene particles with partially reacted azlactone polymer and the ability of the coated organic particle to bind protein (PROCESS IV).

High density porous polyethylene particles (prepared as disclosed in U.S. Pat. No. 4,539,256) were cryogenically ground according to the procedure disclosed in Australian Patent No. 551,446 and then coated with a 5% loading of VDM-60 by a procedure similar to that of Example 30. Untreated and VDM-60 treated particles were evaluated for Protein A binding as previously outlined (Example 26), using 10 mg of particles per tube, 200 µL of Protein A solution, and 500 µL of quenching reagent, PBS, and SDS solution.

Radioactive determinations indicated a 65% increase in covalently bound protein on the VDM-60 treated particles compared to the untreated polyethylene. SDS resistance increased from 24% to 65%, representing a two- to three-fold increase in the relative amounts of covalent protein binding.

EXAMPLE 34

This example shows that graft polymers of VDM and polystyrene can be used to coat glass beads (Corning Glass Works, Corning, N.Y.) (PROCESS IV).

Controlled pore glass (CPG) beads were treated as in Example 30 with sufficient 1 % solution in toluene of a VDM-grafted polystyrene (2% VDM) to result in a 1% loading of the CPG after evaporation. As a control, ungrafted polystrene was also coated onto CPG by a similar procedure. The coated CPGs were then tested for Protein A binding in comparison with the untreated glass material, as previously outlined in Example 26, using 10 mg of support material per tube.

Determination of covalently bound radioactive protein indicated a nine-fold increase of total protein binding to the polystyrene-coated beads over the uncoated beads, with an additional three-fold increase on the VDM-grafted polystyrene coated material. SDS results showed a doubling of percent resistance of the bound protein on the VDM-grafted polystyrene compared with the plain polystyrene-coated beads. These data indicate a significant increase in covalent protein binding as a direct result of the VDM-grafted polymer coated on the glass beads.

EXAMPLE 35

Derivatization of VDM Copolymer Beads and Demonstration of Hydrophobic Interaction Properties VDM copolymer beads from Example 18 were derivatized for 96 hours at room temperature with 0.5M phenethylamine (Aldrich Chem. Co., Milwaukee, Wis.) in 25 mM phosphate buffer, pH 7.5. The beads were washed exhaustively with phosphate buffer, and packed manually into a 0.35 mL Omni glass column (3 mm×5 cm; Rainin Instrument Co., Woburn, Mass.). The column was equilibrated on the FPLC system (Pharmacia Inc., Piscataway, N.J.) with 1.7M ammonium sulfate in 50 mM phosphate buffer, pH 6.8. Ovalbumin (5 mg/mL; Sigma Chem. Co., St. Louis, Mo.) dissolved in the ammonium sulfate buffer was loaded onto the column. At a flow rate of 1.0 mL/min, a 5 mL gradient (1.7M ammonium sulfate to 0.0M in phosphate buffer) was performed to evaluate elution of the protein by hydrophobic interaction. In this example, 0.53 mg of the protein was eluted late in the gradient at 10.45 mL elution volume (1.16M ammonium sulfate), with the remaining protein recovered in the void volume. This result is in contrast to a control column using the identical solvent system, but packed with VDM beads that had been hydrolyzed in phosphate buffer. The control showed no interaction with the ovalbumin, i.e., all of the protein passing unretarded through the hydrolyzed copolymer column at the void volume.

Bovine serum albumin (BSA; Sigma) at 25 mg/mL in ammonium sulfate buffer was injected onto the column and eluted by the same gradient as above, but at a flow rate of 0.3 mL/min. This high concentration (5 mg injection) of protein resulted in 32% of the total protein being eluted at 10.53 mL (1.17M salt), and the rest recovered in the void volume. Upon reinjection, a fraction of the unbound protein from the void volume bound to the column and eluted at 10.49 mL, suggesting that the initial injection had over-loaded the column. These data suggest that as the salt concentration is reduced, the proteins elute from the matrix based on their hydrophobicity. This demonstration indicates the potential application of the VDM copolymer in hydrophobic interaction chromatography.

EXAMPLE 36

Demonstration of Ion Exchange Properties

VDM copolymer beads from Example 18 were derivatized with 0.7M taurine (Aldrich Chem., Milwaukee, Wis.) in 25 mM phosphate buffer, pH 7.5, for 72 hours at room temperature. The excess reagent was rinsed from the beads with buffer before packing in a 0.35 mL Omni glass column (3 mm×5 cm). The column was equilibrated with 50 mM acetic acid, pH 5.0. BSA was dissolved in the equilibration buffer, and 0.8 mg was injected onto the column. After loading the protein in 5 mL of equilibration buffer at a flow rate of 0.5 mL/min, a 25 mL salt gradient from 0 to 2M NaCl (in 50 mM acetate, pH 5.0) was applied for ion exchange elution. As detected by UV absorbance readings at 280 nm, 0.54 mg of the BSA eluted from the column at an elution volume of 8.8 mL. The remaining protein was recovered in the void volume.

The above protocol was performed with bovine IgG (Sigma) as the experimental protein to evaluate differences in elution between two proteins. After loading 0.68 mg IgG, approximately 0.52 mg (64%) was eluted at 8.4 mL, with the remaining IgG recovered in the void volume. These results correlate with previous experiments using commercial ion exchange matrices, in which IgG eluted slightly before BSA on a Mono S column (Pharmacia Co., Piscataway, N.J.).

A mixture of the above two proteins was resolved using the taurine-azlactone column when it was injected onto the column and eluted at 0.2 mL/min according to the following multiple gradient: a 30 mL gradient from 0 to 0.30M NaCl, followed by a 15 mL gradient to 1.0M NaCl, and final cleansing of bound protein with 2M NaCl. The proteins eluted in two main peaks at 17.8 mL (0.13M NaCl) and at 21.5 mL (0.16M NaCl). These elution volumes vary from the previous examples, due to the change in flow rate.

EXAMPLE 37

Demonstration of Anion Exchange Properties of Azalactone Beads

VDM polymer beads from Example 18 were reacted with an excess of 4-dimethylamino-1-butylamine in acetone for 12 hours at reflux. Following filtration and washing with acetone to remove unreacted amine, the beads were dried under vacuum at 60 degrees C. The beads were then packed into a 2.0 mL glass column, 5 mm×10 cm (Pharmacia Fine Chemicals, Uppsalla, Sweden), and equilibrated with 20 mM tris(hydroxymethyl)aminomethane (Tris), pH 8.0. BSA and bovine IgG were injected onto the column and eluted with a 20 mL gradient from 0 to 2M NaCl, 20 mM Tris, pH 8.0. The retention volumes for the proteins were 17.0 and 21.7, respectively, with a void volume of 4.1 mL. This demonstrates the use of cationic derivative of the VDM polymer beads for anion exchange separations.

EXAMPLE 38

Demonstration of Size Exclusion Properties

VDM polymer beads from Example 18 were hydrolyzed in 10 mM phosphate buffer at pH 7.5 for >72 hours at room temperature. The beads were packed in a 2 mL glass column, 5 mm×10 cm, and equilibrated in 50 mM sodium sulfate in phosphate buffer (10 mM), pH 7.2. The materials shown in TABLE IX, below, were dissolved in water and filtered (0.2 μm) prior to injection onto the column:

TABLE IX

Separation of Biological Molecules by Size Exclusion Using Porous Polymer Beads

| Material | MW (Daltons) | Elution Volume |
| --- | --- | --- |
| blue dextran TM | 2,000,000 | 1.45 mL |
| thyroglobulin | 670,000 | 1.53 |
| catalase | 247,000 | 1.63 |
| bovine serum albumin | 69,000 | 1.80 |
| myoglobin | 17,000 | 1.98 |
| vitamin B-12 | 1,355 | 2.25 |
| 6M sodium sulfate | 142 | 2.60 |

Each material (100 μL) was loaded onto the column and eluted in the running buffer at a flow rate of 0.2 mL/min. Detection of the elution volume was by UV absorbance at 280 nm. The 6M sodium sulfate provides an absorbance deflection due to a refractive index change caused by the increased salt concentration, and provides a very low molecular weight non-protein marker.

The graphed results show a linear relationship between the log of the molecular weight and the elution volume. These data are indicative of wide ranging size exclusion properties of the hydrolyzed VDM polymer. Based on this standard curve, this particular preparation of azlactone copolymer beads can be used for size exclusion chromatography over a molecular weight range of 4 log units (100 to 1,000,000).

EXAMPLE 39

Size Exclusion Characteristics of Derivatized VDM

VDM copolymer from Example 18 was derivatized with two amine reagents of short chain lengths for further size exclusion studies. The beads were exposed to either 2M ethylamine in phosphate buffer (25 mM, pH 7.5) or 0.5M butylamine (in the same buffer system) for at least 72 hours at room temperature. The excess amines were removed by rinsing in buffer, and individual 5 mm×10 cm columns were prepared. Blue dextran, thyroglobulin, catalase, and bovine serum albumin were loaded onto the columns and eluted as described in Example 38. The results again demonstrate a linear relationship between the log of the molecular weight and the elution volume.

EXAMPLE 40

Demonstration of Reverse Phase Chromatography

Azlactone polymer beads from Example 18 were derivatized by 1M octylamine in phosphate buffer (25 mM), pH 7.2, for 72 hours at room temperature. The beads were washed free of excess alkyl amine with buffer and were packed in an Omni 3 mm×5 cm glass chromatography column. The 0.35 mL column was equilibrated in 1.7M ammonium sulfate (pH 7.0). Myoglobin was dissolved in the equilibration buffer and 1.25 mg was loaded onto the column. Elution with a decreasing salt gradient of ammonium sulfate as in Example 35 did not result in any protein recovery. The use of typical protein reverse phase elution conditions, a 30 mL gradient of 1% trifluoroacetic acid (TFA) in water to 1% TFA in 70% methanol, resulted in recovery of the protein. The demonstration was repeated with polymer beads reacted with 0.5M methylamine (C1), 2M ethylamine (C2) and 0.5M butylamine (C4) with similar results.

Using the beads with C8 groups attached, injections of myoglobin, BSA, and lysozyme were made and eluted with a 30 mL gradient from 1% TFA in water to 1% TFA in 70% methanol at a flow rate of 0.1 mL/min. The elution profiles are summarized in Table X.

TABLE X

Reverse Phase Separations of Proteins Using Octylamine-Derivatized Copolymer Beads

| Protein | Peak Elution (mL) | Integrated Area (% of Total) |
|---|---|---|
| Myoglobin | 0.61 | 18 (Void volume) |
| | 6.1 | 28 |
| | 36.3 | 50 |
| BSA | 0.67 | 8 (Void volume) |
| | 26.8 | 18 |
| | 31.8 | 30 |
| | 36.2 | 43 |
| Lysozyme | 0.72 | 9 (Void volume) |
| | 33.8 | 86 |

The differences in these elution profiles are indicative of the differences in the size and hydrophobic nature of these proteins and demonstrate the use of VDM beads derivatized with C1 to C8 groups in reverse phase chromatography.

EXAMPLE 41

Reverse Phase Chromatography of Low Molecular Weight Materials

VDM beads of Example 18 were reacted with excess n-hexadecylamine (C16) in diethyl ether for an hour. The unreacted amine was removed by filtration and washing with diethyl ether. The derivatized beads were then dispersed in methanol and packed into a 4.6×100 mm stainless steel HPLC column. After equilibrating in 45/55 methanol/water, injections of small molecule organics were made and eluted at 0.25 mL/min with UV detection at 280 nm. Table XI summarizes the retention times and further demonstrates the use of alkylamine derivatized VDM polymer beads as reverse phase chromatography supports.

TABLE XI

Reverse Phase Separation of Low Molecular Weight Materials

| Compound | Retention (Vol/void vol) |
|---|---|
| uracil | 1.0 |
| benzophenone | 1.57 |
| nitrobenzene | 2.15 |

EXAMPLE 42

Coating of Azlactone Monomer onto Polystyrene Wells

2-Vinyl-4,4-dimethyl azlactone monomer (VDM) was formulated with 0.25 g by weight of a photoinitiator (IRGACURE TM 651 (Ciba Geigy)), then painted on the surface of polystyrene microtiter wells (Immulon TM II, Dynatech, Springfield, Va.). The wells were then irradiated under a nitrogen atmosphere using a bank of four fluorescent blacklight tubes (GTE Sylvania, Inc.) for 30 minutes. This resulted in the polymerization of the azlactone monomer on the surface of the wells. Other monomers such as 4-isopropenyl-4,4-dimethylazlactone (IDM) can be coated in a similar manner.

EXAMPLE 43

Coating Azlactone-Functional Copolymers Onto Polystyrene Wells

Copolymers of VDM and methyl methacrylate (MMA) were prepared by standard free radical solution polymerization techniques. Samples of copolymers containing VDM/MMA ratios (mole/mole) of 85:15, 70:30, and 50:50 were each diluted with solids in ethyl acetate. Coating of microtiter wells was accomplished by placing 3 drops of polymer solution into each well using a disposable pipette, followed by evaporation in a circulating air oven at 60 degrees C. for 30 minutes. Alternatively, copolymer solution was painted onto the wells, followed by solvent evaporation.

EXAMPLE 44

Use of Polystyrene Wells for Improved Immunoassays

Evaluation of the modified surfaces of the wells of EXAMPLE 42 was carried out by adding aqueous solutions of mouse IgG (Sigma Chemical) or anti-goat IgG (Cooper-BioMedical, Malvern, Pa.) at 50 µg/mL in PBS, pH 7.0, to 48 wells and incubating them at room temperature for 2 hours. The solutions were aspirated and a fixing solution of BSA (2.5 mg/mL) and sucrose (5%) in PBS was incubated for 30 minutes. The coated wells were then aspirated and dried. A similar number of of unmodified wells were coated by this procedure.

The amount of bound protein was evaluated by adding enzyme-labeled reagents, anti-mouse IgG-alkaline phosphatase and goat IgG-horseradish peroxidase to mouse IgG and anti-goat IgG treated wells, respectively, incubating for 1 hour and washing the wells three times with a pH 7.5 buffered non-ionic surfactant solution. After adding the appropriate enzyme substrates, the color produced by the bound enzyme-labeled reagents was measured. The data from these wells are summarized in TABLE XII below.

TABLE XII

Binding of Antibodies to Azlactone Copolymer-Coated Microtiter Wells

| Well Treatment | Absorbance | SD* | CV**(%) |
|---|---|---|---|
| Anti-IgG | | | |
| Control (No Treatment) | 0.078 | 0.029 | 37 |
| Azlactone Treated | 0.095 | 0.023 | 25 |
| IgG | | | |
| Control | 0.664 | 0.082 | 12 |
| Azlactone Treated | 1.161 | 0.115 | 9 |

*SD = standard deviation
**CV = coefficient of variation (SD/mean)

Wells treated with mouse IgG produced nearly 75% more signal than untreated wells while the anti-goat IgG wells produced over a 20% increase in coupled signal. The coefficient of variation of the modified wells were about one-third less than those of the untreated wells.

The data of TABLE XII indicates that both the amount of protein bound and the reproducibility of the treatment are increased over the normal passive adsorption technique.

EXAMPLE 45

Improved Binding of Allergenic Proteins to Coated Polystyrene Wells

Perennial ryegrass (PRG) extract and chymopapain (CP) (3M Diagnostic Systems, Santa Clara, Calif.) were isotopically labeled with I-125 and incubated in control (untreated) and VDM/MMA-treated polystyrene microtiter wells prepared as in Example 43 for 2 hours at ambient temperature. Radioactive solution was removed by aspiration and unreacted/unbound sites on the surface were blocked by incubation with serum albumin for 1 hour. The residual radioactivity of the dried wells was determined and the corresponding amounts of bound protein calculated as shown in TABLE XIII below.

TABLE XIII

Binding of Allergenic Proteins to Coated and Control Polystyrene Wells

| Sample | Bound Protein (ng) | SD | CV(%) |
|---|---|---|---|
| PRG | | | |
| Control | 66 | 2.2 | 3.4 |
| VDM | 79 | 3.8 | 4.8 |
| CP | | | |
| Control | 45 | 2.2 | 4.8 |
| VDM | 56 | 2.6 | 4.7 |

The data of TABLE XIII show that VDM-coated polystyrene wells bound 20–25% more allergen protein with similar precision than the Control.

EXAMPLE 46

Increased Irreversible Binding of Allergenic Proteins to Coated Polystyrene Wells Microtiter test wells coated with I-125-labeled-allergens, as in EXAMPLE 45, were incubated with 0.1% SDS at 37° C. or in phosphate buffer at ambient temperature. After 4 hours solutions were removed by aspiration and rinsed twice with deionized water, and the residual bound I-125 was rinsed twice with deionized water, and the residual bound I-125 was determined. The percent protein remaining is presented below in TABLE XIV.

TABLE XII

Increased Resistance of Azlactone-Bound Protein to Solubilization by Denaturant

| | % Protein Remaining | | | |
|---|---|---|---|---|
| | PRG* | | CP** | |
| SAMPLE | BUFFER | SDS | BUFFER | SDS |
| Control | 83 | 43 | 74 | 37 |
| 50/50 VDM/MMA | 85 | 64 | 82 | 68 |
| 70/30 VDM/MMA | 85 | 64 | 85 | 73 |
| 85/15 VDM/MMA | 86 | 67 | 83 | 73 |
| IDM | 83 | 45 | 77 | 49 |

*PRG = perennial rye grass
**CP = chymopapain

With the possible exception of the isopropenyl derivatives with PRG, the data of TABLE XIV show there is considerably higher residual binding in azlactone-treated wells than in controls indicating covalent binding of allergen protein.

COMPARATIVE EXAMPLE 47

The following Example is an attempt to prepare azlactone-functional beads by a procedure similar to that of EXAMPLE 3 of U.S. Pat. No. 4,070,348.

Heptane (42 g), perchloroethylene (84 g) and benzoyl peroxide (0.5 g) were placed in a 500 mL round bottom flask. Acrylamide (15 g), VDM (15 g), ethylene glycol dimethacrylate (0.76 g), and polymeric stabilizer (0.025 g) were dissolved in DMF (20 g) and this solution was then added to the reaction flask at room temperature. The polymeric stabilizer used was an isobutylacrylate/n- butylacrylate/VDM (45:45:10) copolymer which had been reacted with choline salicylate by a procedure similar to that of EXAMPLE 24A. The monomer phase was distributed in the organic phase by stirring at 350 rpm and was purged with $N_2$ for 45 minutes. With external cooling, the polymerization was initiated by the addition of dimethylaniline (0.25 g). Within three minutes, the monomer mixture had separated out as a large, crosslinked mass around the stirrer shaft. No beads were evident.

EXAMPLE 48 (Comparative)

The following is an attempt to prepare an azlactone-functional bead according to the teachings of U.S. Pat. No. 4,070,348. The reaction was carried out using the same ingredients and their amounts as specified in EXAMPLE 25 of U.S. Pat. No. 4,070,348, except that VDM was substituted for glycidyl acrylate. Again, a crosslinked polymer mass separated within two minutes of initiation of the reaction. No beads were evident.

Various modifications and alterations of this invention will become apparent to those skilled in the art without departing from the scope and spirit of this invention, and it should be understood that this invention is not to be unduly limited to the illustrative embodiments set forth herein.

We claim:

1. A polymeric adduct support having units of the formula

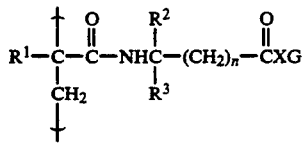

wherein
$R^1$ is H or $CH_3$,
$R^2$ and $R^3$ each independently is an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or $R^2$ and $R^3$ taken together with the carbon to which they are joined can form a carbocyclic ring containing 4 to 12 ring atoms,
n=0 or 1,
X is —O—, —S—, —NH—, or —$NR^4$— wherein $R^4$ is alkyl or aryl, and
G is the residue of HXG which performs the adsorbing, complexing, catalyzing, separating, or reagent function of the adduct supports, said adduct support having in the range of 0 to 99 molar parts of crosslinking monomer incorporated therein, and said adduct support being a bead.

2. The adduct support according to claim 1 wherein $R^1$ is hydrogen, $R^2$ and $R^3$ are methyl, and $n=0$.

3. The adduct support according to claim 1 wherein HXG is selected from the group consisting of adsorbants, biologically active substances, catalysts, reagents, and dyes.

4. The adduct support according to claim 1 wherein said biologically active substance is selected from the group consisting of antibodies, antigens, enzymes, cofactors, inhibitors, lectins, hormones, receptors, coagulation factors, amino acids, histones, vitamins, drugs, cell surface markers, and substances which interact with any of the foregoing.

5. The adduct support according to claim 1 which is a complexing agent.

6. The adduct support according to claim 1 which is a chromatographic support.

7. The adduct support according to claim 1 which is a catalyst.

8. The adduct support according to claim 1 which is a polymeric reagent.

9. The adduct support according to claim 1 which is an adsorbant.

10. The support according to claim 9 having in the range of 0.1 to 99 molar parts of crosslinking monomer incorporated therein.

* * * * *

UNITED STATES PATENT AND TRADEMARK OFFICE
CERTIFICATE OF CORRECTION

PATENT NO. : 5,292,840
DATED : March 8, 1994
INVENTOR(S) : Steven M. Heilmann et al.

It is certified that error appears in the above-indentified patent and that said Letters Patent is hereby corrected as shown below:

Col. 7, lines 60-61, "N-(3-methacrylamidopropyl)-N,N,N-trimerhylammonium" should be -- N-(3-methacrylamidopropyl)-N,N,N-trimethylammonium --.

Col. 11, lines 35-42, replace that part of the Chemical Equation with --

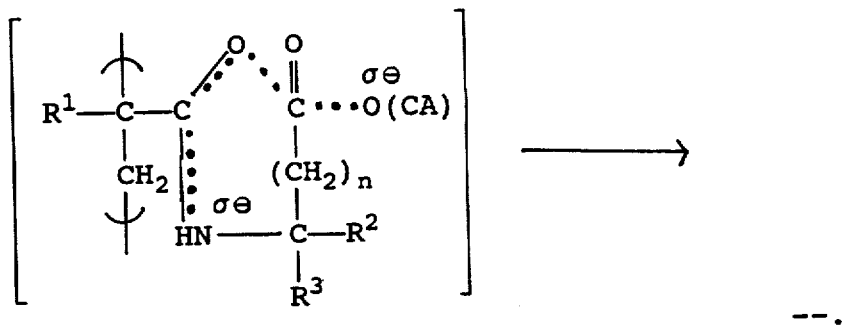

--.

Col. 13, lines 7-8, "inacetic anhydride" should read -- in acetic anhydride --.

Col. 18, line 16, "poIymer" should be -- polymer --.

Col. 18, line 21, "is -novel" should be -- is novel --.

Col. 20, line 12, after "material" insert -- . --.

UNITED STATES PATENT AND TRADEMARK OFFICE
CERTIFICATE OF CORRECTION

PATENT NO. : 5,292,840
DATED : March 8, 1994
INVENTOR(S) : Steven M. Heilmann et al.

It is certified that error appears in the above-indentified patent and that said Letters Patent is hereby corrected as shown below:

Col. 21, line 67, "NaAMA After" should be -- NaAMA. After --.

Col. 24, line 60, "30-36 ml" should be -- 30-36 mg --.

Col. 25, line 45, "buffer Human" should be -- buffer. Human --.

Col. 25, line 50, "protein Finally" should be -- protein. Finally --.

Col. 26, line 22, "less than torr" should be -- less than 1 torr --.

Col. 27, line 67, "of g/mL" should be -- of 250 µg/mL --.

Col. 29, line 46, "solution The" should be -- solution. The --.

Col. 30, line 17, "at degrees" should be -- at 135 degrees --.

Col. 30, lines 27-28, "Approximately mg" should be -- Approximately 10 mg --.

Col. 31, lines 28-29, "Filter-Pure™ 5 Nylon-66" should be -- Filter-Pure™ Nylon-66 --.

Col. 32, line 42, "Omni glass" should be -- Omni™ glass --.

UNITED STATES PATENT AND TRADEMARK OFFICE
CERTIFICATE OF CORRECTION

PATENT NO. : 5,292,840
DATED : March 8, 1994
INVENTOR(S) : Steven M. Heilmann et al.

It is certified that error appears in the above-indentified patent and that said Letters Patent is hereby corrected as shown below:

Col. 32, line 49, "a 5 mL" should be -- a 15 mL --.

Col. 33, line 18, "Omni glass" should be -- Omni™ glass --.

Col. 36, line 15, "with solids" should be -- with 10% solids --.

Signed and Sealed this

Thirteenth Day of December, 1994

BRUCE LEHMAN

Attest:

Attesting Officer

Commissioner of Patents and Trademarks